(12) United States Patent
Davis

(10) Patent No.: US 8,067,042 B1
(45) Date of Patent: Nov. 29, 2011

(54) MEGESTROL ACETATE PRODUCTS, METHOD OF MANUFACTURE, AND METHOD OF USE

(75) Inventor: Matthew William Davis, Erwinna, PA (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 98 days.

(21) Appl. No.: 12/272,873

(22) Filed: Nov. 18, 2008

Related U.S. Application Data

(60) Provisional application No. 60/988,968, filed on Nov. 19, 2007, provisional application No. 60/990,319, filed on Nov. 27, 2007.

(51) Int. Cl.
*A61K 36/38* (2006.01)
*A61K 36/752* (2006.01)

(52) U.S. Cl. ........................ 424/730; 424/736

(58) Field of Classification Search .................. None
See application file for complete search history.

(56) References Cited

U.S. PATENT DOCUMENTS

| | | | |
|---|---|---|---|
| 4,760,053 A | 7/1988 | Labrie | |
| 2003/0108484 A1* | 6/2003 | Leyland-Jones | 424/9.2 |

OTHER PUBLICATIONS

Zhang et al, Screening study of the inhibitory effects 17 steroides on 6 major cytochrome p450 isoenzymes, Drug metabolism reviews 92006) 38 (3): 99-100.*

Kornblith et al, Effect of megestrol acetate on quality of life in a dose-response trial in women with advanced breast cancer, Journal of Clinical Oncology, 11 (11), 1993: 2081-2089.*

Williams et al, Crystal structures of human cytochrome P450 3A4 bound to metyrapone and progesterone, Science (New York, N.Y.), (Jul. 30, 2004) vol. 305, No. 5684, pp. 683-686.*

Introduction of Megestrol acetate from Wikipedia, accessed on Nov. 13, 2010, pp. 1-2.*

Nelson, David R. et al., "P450 Superfamily: Update on New Sequences, Gene Mapping, Accession Numbers and Nomenclature"; Pharmacogenetics; vol. 6; 1996; pp. 1-42.

"Drug Interaction Studies—Study Design, Data Analysis, and Implications for Dosing and Labeling; Preliminary Concept Paper"; Oct. 1, 2004; available @ http://www.fda.gov/ohrms/dockets/ac/04/briefing/2004-4079B1_04_Topic2-TabA.pdf.

* cited by examiner

*Primary Examiner* — Qiuwen Mi
(74) *Attorney, Agent, or Firm* — Cantor Colburn LLP

(57) ABSTRACT

Disclosed herein is a method of using megestrol acetate. In one embodiment, the method comprises informing a user that megestrol acetate is metabolized by a cytochrome p450 isozyme. In another embodiment, the method comprises obtaining megestrol acetate from a container associated with published material providing information is metabolized by a cytochrome p450 isozyme. Also disclosed are articles of manufacture comprising a container containing a dosage form of megestrol acetate, wherein the container is associated with published material informing that megestrol acetate is metabolized by a cytochrome p450 isozyme, a method of treatment, and a method of manufacturing a megestrol acetate product.

6 Claims, No Drawings

MEGESTROL ACETATE PRODUCTS, METHOD OF MANUFACTURE, AND METHOD OF USE

CROSS REFERENCE TO RELATED APPLICATION

This application claims the benefit of U.S. Provisional Application Ser. No. 60/988,968, filed Nov. 19, 2007 and of U.S. Provisional Application Ser. No. 60/990,319 filed Nov. 27, 2007, each of which is hereby incorporated by reference in its entirety.

BACKGROUND

This application relates to megestrol acetate products for therapeutic purposes, and in particular to improved methods of use of megestrol acetate.

Megestrol acetate, also known as 17 α-acetyloxy-6-methylpregna-4,6-diene-3,20-dione, is a synthetic progestin with progestational effects similar to those of progesterone. It is used in a variety of situations including treatment of breast cancer, contraception, and hormone replacement therapy in post-menopausal women. It is also used in abortion, endometriosis, and menstrual disorders. Additionally, megestrol acetate is frequently prescribed as an appetite enhancer for patients in a wasting state, such as HIV wasting, cancer wasting, or anorexia. In combination with ethynyl estradiol it acts as an oral contraceptive. It is also administered to subjects after castration.

Megestrol acetate is currently supplied in the United States as oral tablets and oral suspensions. Oral tablets contain 20 mg or 40 mg megestrol acetate. Inactive ingredients are acacia, calcium phosphate, FD&C Blue No. 1 Aluminum Lake, lactose, magnesium stearate, silicon dioxide colloidal, and starch. Oral suspensions contain 40 mg or 125 mg micronized megestrol acetate per milliliter. Inactive ingredients include alcohol (max 0.06% v/v from flavor), artificial lime flavor, citric acid monohydrate, docusate sodium, glycerin, natural and artificial lemon flavor, purified water, sodium benzoate, sodium citrate dihydrate, sucrose and xanthan gum.

Megestrol acetate oral tablets are specifically indicated for the palliative treatment of advanced carcinoma of the breast or endometrium (i.e., recurrent, inoperable, or metastatic disease). Additionally, the megestrol acetate oral suspension is indicated for the treatment of anorexia, cachexia, or an unexplained, significant weight loss in patients with a diagnosis of acquired immunodeficiency syndrome (AIDS). Megestrol acetate is also disclosed for treating sex steroid dependent cancers (U.S. Pat. No. 4,760,053).

While the precise mechanism by which megestrol acetate produces its antineoplastic effects against endometrial carcinoma is unknown at the present time, inhibition of pituitary gonadotrophin production and resultant decrease in estrogen secretion may be factors. There is evidence to suggest a local effect as a result of the marked changes brought about by the direct instillation of progestational agents into the endometrial cavity. The antineoplastic action of megestrol acetate on carcinoma of the breast is effected by modifying the action of other steroid hormones and by exerting a direct cytotoxic effect on tumor cells. In metastatic cancer, hormone receptors may be present in some tissues but not others. The receptor mechanism is a cyclic process whereby estrogen produced by the ovaries enters the target cell, forms a complex with cytoplasmic receptor and is transported into the cell nucleus. There it induces gene transcription and leads to the alteration of normal cell functions. Pharmacologic doses of megestrol acetate not only decrease the number of hormone-dependent human breast cancer cells but also is capable of modifying and abolishing the stimulatory effects of estrogen on these cells. It has been suggested that progestins may inhibit in one of two ways: by interfering with either the stability, availability, or turnover of the estrogen receptor complex in its interaction with genes or in conjunction with the progestin receptor complex, by interacting directly with the genome to turn off specific estrogen-responsive genes.

Several investigators have reported on the appetite enhancing property of megestrol acetate and its possible use in cachexia. The precise mechanism by which megestrol acetate produces effects in anorexia and cachexia is unknown at the present time.

One of the most important groups of Phase I metabolic enzymes are the cytochrome p450 monooxygenase system enzymes. The cytochrome p450 enzymes are a highly diverse superfamily of enzymes. NADPH is required as a coenzyme and oxygen is used as a substrate. Each enzyme is termed an isoform or isozyme since each derives from a different gene.

Many members of the cytochrome p450 family are known to metabolize active agents in humans. Active agent interactions associated with metabolism by cytochrome p450 isoforms generally result from enzyme inhibition or enzyme induction. Enzyme inhibition often involves competition between two active agents for the substrate-binding site of the enzyme, although other mechanisms for inhibition exist. Enzyme induction occurs when an active agent activates an enzyme or stimulates the synthesis of more enzyme protein, enhancing the enzyme's metabolizing capacity.

Cytochrome p450 isozymes identified as important in active agent metabolism are CYP1A2, CYP2A6, CYP2B6, CYP2C8, CYP2C9, CYP2C19, CYP2D6, CYP2E1, and CYP3A4. Examples of cytochrome p450 enzymes known to be involved in active agent interactions are the CYP3A subfamily, which is involved in many clinically significant active agent interactions, including those involving non-sedating antihistamines and cisapride, and CYP2D6, which is responsible for the metabolism of many psychotherapeutic agents, such as thioridazine. CYP1A2 and CYP2E1 enzyme are involved in active agent interactions involving theophylline. CYP2C9, CYP1A2, and CYP2C19 are involved in active agent interactions involving warfarin. Phenyloin and fosphenyloin are metabolized by CYP2C9, CYP2C19, and CYP3A4.

Additionally, several cytochrome p450 isozymes are known to be genetically polymorphic, leading to altered substrate metabolizing ability in some individuals. Allelic variants of CYP2D6 are the best characterized, with many resulting in an enzyme with reduced, or no, catalytic activity. Gene duplication also occurs. As a result, four phenotypic subpopulations of metabolizers of CYP2D6 substrates exist: poor (PM), intermediate (IM), extensive (EM), and ultrarapid (UM). The genetic polymorphisms vary depending on the population in question. For example, Caucasian populations contain a large percentage of individuals who are poor metabolizers, due to a deficiency in CYP2D6—perhaps 5-10% of the population, while only 1-2% of Asians are PMs. CYP2C9, which catalyzes the metabolism of a number of commonly used active agents, including that of warfarin and phenyloin, is also polymorphic. The two most common CYP2C9 allelic variants have reduced activity (5-12%) compared to the wild-type enzyme. Genetic polymorphism also occurs in CYP2C19, for which at least 8 allelic variants have been identified that result in catalytically inactive protein. About 3% of Caucasians are poor metabolizers of active agents metabolized by CYP2C19, while 13-23% of Asians are poor metabolizers of active agents metabolized by CYP2C19. Allelic variants of CYP2A6 and CYP2B6 have also been identified as affecting enzyme activity. At least one inactive CYP2A6 variant occurs in Caucasians at a frequency of 1-3%, resulting in a PM phenotype. A whole gene deletion has been identified in a Japanese population, with an allelic frequency of 21%; homozygotes in this mutation show a PM phenotype. For CYP2B6, about 3-4% of Caucasians have a polymorphism producing a PM phenotype.

Active agent interactions present a health risk to patients and a medical challenge for all medical care workers. Various studies of adverse reactions from exposure to active agents have found that 6.5-23% of the adverse reactions result from active agent interactions. Unfortunately, each year a number of deaths occur as the direct result of patients taking a new prescription pharmaceutical product in combination with their existing medication regimen. By understanding the unique functions and characteristics of Phase I and Phase II metabolic enzymes, such as the cytochrome p450 enzyme superfamily, medical care workers such as physicians and pharmacists may better avoid or safely manage active agent interactions and may better anticipate or explain an individual's response to a particular therapeutic regimen.

There accordingly remains a need in the art for improved methods for the administration and use of megestrol acetate, in particular methods that take into account the effects of megestrol acetate metabolism by cytochrome P450 isozymes.

SUMMARY

Disclosed herein are methods of using megestrol acetate. Megestrol acetate can be used in the prevention or treatment of various diseases or conditions, including, for example, treatment of breast cancer, contraception, and hormone replacement therapy in post-menopausal women. It is also used in abortion, endometriosis, menstrual disorders, and sex steroid dependent cancers. Additionally, megestrol acetate is frequently prescribed as an appetite enhancer for patients in a wasting state, such as HIV wasting, cancer wasting, or anorexia. When used in combination with ethynyl estradiol megestrol acetate acts as an oral contraceptive. It is also administered to subjects after castration.

In one embodiment, the method comprises administering megestrol acetate to a patient in need thereof; and monitoring the patient during administration of megestrol acetate if a substance that is a known inhibitor or a known inducer of CYP 3A4 is coadministered to the patient.

In one embodiment, the method comprises determining for a patient to whom megestrol acetate is going to be administered or is being administered whether a substance that is currently being or will be administered to the patient is an inhibitor or an inducer of CYP3A4; and determining risk for the patient of an adverse event during coadministration of megestrol acetate and the substance resulting from inhibition or induction of megestrol acetate metabolism by CYP3A4 during coadministration of megestrol acetate and the substance.

In one embodiment, the method comprises administering megestrol acetate to a patient in need of megestrol acetate therapy; determining that a substance that is an inhibitor or an inducer of CYP3A4 is administered to the patient; determining that the patient experiences an adverse reaction associated with elevated or decreased megestrol acetate plasma concentration during administration of megestrol acetate and the substance; and adjusting administration of megestrol acetate or the substance to the patient to reduce severity of or eliminate the adverse reaction.

In one embodiment, the method comprises determining that a patient in need of megestrol acetate therapy is taking a substance that is a known inhibitor or a known inducer of CYP3A4; and adjusting administration to the patient of megestrol acetate or the substance to avoid an adverse event associated with a change in the metabolism of megestrol acetate.

In one embodiment, the method comprises informing a patient that megestrol acetate is metabolized by CYP3A4

In one embodiment, the method comprises administering megestrol acetate and a substance which is an inhibitor or an inducer of CYP3A4 to a patient; and altering dosing of the substance or megestrol acetate for the patient to minimize a side effect, an adverse event, or an active agent interaction.

In one embodiment, the method comprises informing a user that administration of an inhibitor of CYP3A4 can reduce metabolism of megestrol acetate; or that administration of an inducer of CYP3A4 can increase metabolism of megestrol acetate.

In one embodiment, the method comprises informing a user that administration of megestrol acetate with a substance that is an inhibitor of CYP3A4 can result in increased megestrol acetate plasma concentration or a megestrol acetate associated toxicity.

In one embodiment, the method comprises informing a user that administration of megestrol acetate with a substance that is an inducer of CYP3A4 can result in a decreased megestrol acetate plasma concentration or reduced efficacy of megestrol acetate.

In one embodiment, the method comprises determining that a patient in need of megestrol acetate therapy is taking a substance that is a known inhibitor of CYP3A4, and adjusting administration to the patient of megestrol acetate or the substance to avoid an adverse event associated with megestrol acetate.

In one embodiment, the method comprises determining that a patient in need of megestrol acetate therapy is taking a substance that is a known inducer of CYP3A4, and adjusting administration to the patient of megestrol acetate or the substance to avoid a subtherapeutic outcome with megestrol acetate.

In another embodiment, the method comprises obtaining megestrol acetate from a container associated with published material providing information that megestrol acetate is metabolized by cytochrome p450 3A4.

In an embodiment, the method comprises determining that a substance that is a known inducer or a known inhibitor of CYP3A4 is administered to a patient in need of megestrol acetate therapy; and dispensing megestrol acetate to the patient in a container associated with published material providing information that megestrol acetate is metabolized by CYP3A4.

Also disclosed herein are methods of manufacturing a megestrol acetate product.

In one embodiment, the method comprises packaging a megestrol acetate dosage form with published material providing information that megestrol acetate is metabolized by cytochrome p450 3A4.

Also disclosed herein are articles of manufacture comprising a container containing a dosage form of megestrol acetate.

In one embodiment, the container is associated with published material informing that megestrol acetate is metabolized by cytochrome p450 3A4.

These and other embodiments, advantages and features of the present invention become clear when detailed description and examples are provided in subsequent sections.

DETAILED DESCRIPTION

Disclosed herein are methods of using megestrol acetate and megestrol acetate products. The inventors have determined certain effects of megestrol acetate on the activity of a cytochrome P450 isozyme and risks associated with administration of megestrol acetate with another substance, specifically another active agent, resulting from these effects. With the knowledge of the particular information, a medical care worker can better avoid or safely manage an active agent interaction in a patient between megestrol acetate and the substance, and its resultant effects on efficacy or safety of megestrol acetate or the substance. Specifically, knowledge of the particular information permits the administration of megestrol acetate or the substance to a patient to be optimized for the patient by a medical care worker to provide safe use of megestrol acetate, while oftentimes reducing or minimizing side effects, adverse events, or interactions with another substance. Knowledge of the particular information permits a medical care worker to use megestrol acetate to treat a patient that is taking another substance such that a side effect, an adverse reaction, or an active agent interaction between megestrol acetate and the substance can be avoided in the patient. The particular information allows proper dosing, dispensing, and administration of megestrol acetate or the substance to the patient by the patient's medical care worker to avoid, or reduce risk of occurrence of, a side effect, an adverse reaction, or an active agent interaction between megestrol acetate and the substance and alerts the patient's medical care worker to the need to monitor the patient for symptoms of a side effect, an adverse reaction, or an active agent interaction between megestrol acetate and the substance.

Megestrol acetate therapy can be considered optimal when effective plasma levels are reached when required. In addition, peak plasma values ($C_{max}$) should be as low as possible so as to reduce the incidence and severity of possible side effects.

Enzymes involved in Phase I and Phase II active agent metabolism, such as the cytochrome p450 isozymes, respond to the constantly changing types and amounts of substrates they encounter. For example, changes in active agent metabolism due to competition for the same cytochrome P450 isoform can change the clinical effectiveness or safety of an active agent by altering the plasma concentration of the active agent or its metabolite(s). Similarly, inhibition or induction of the cytochrome P450 isoform that metabolizes a particular active agent can change the clinical effectiveness or safety of that active agent. Therefore, for any cytochrome P450 for which megestrol acetate acts as a substrate, inhibitor, or inducer, the administration of megestrol acetate with a substance that is a substrate, inhibitor, or inducer of that cytochrome P450 can affect the metabolism of megestrol acetate or the substance. For the case in which the substance is a narrow therapeutic index active agent, such as warfarin or phenyloin, too little of the active agent in the blood stream can lead to insufficient therapeutic activity, while a too large dose of the active agent can lead to excessive therapeutic activity or toxicity, either of which can be detrimental to the patient.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

An "active agent" means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are contemplated herein. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of megestrol acetate or other active agent may be employed either alone or in combination.

"Active agent interaction" refers to a change in the metabolism or the pharmacology of an active agent in a patient that can occur with co-administration of a second active agent. A "potential active agent interaction" refers to an active agent interaction between two active agents that is theoretically possible based on knowledge that one of the active agents is metabolized by a given cytochrome p450 isozyme and that the second of the active agents is a substrate, inhibitor, or inducer of that cytochrome p450 isozyme.

"Administering megestrol acetate with a substance" or "administering megestrol acetate and a substance", or "co-administering megestrol acetate and a substance" means megestrol acetate and the substance are administered simultaneously in a single dosage form, administered concomitantly in separate dosage forms, or administered in separate dosage forms separated by some amount of time that is within the time in which both megestrol acetate and the substance are within the blood stream of a patient. The megestrol acetate and the substance need not be prescribed for a patient by the same medical care worker. The substance need not require a prescription. Administration of megestrol acetate or the substance can occur via any appropriate route, for example, oral tablets, oral capsules, oral liquids, inhalation, injection, suppositories or topical contact.

"Adverse event" means any untoward medical occurrence in a patient administered an active agent and which does not necessarily have to have a causal relationship with this treatment. An adverse event (AE) can therefore be any unfavorable and unintended sign (including an abnormal laboratory finding, for example), symptom, or disease temporally associated with the use of the active agent, whether or not considered related to the active agent.

"Adverse reaction" means a response to an active agent which is noxious and unintended and which occurs at doses normally used in humans for prophylaxis, diagnosis, or therapy of disease or for modification of physiological function. The unintended response can be an unexpected diminished or enhanced pharmacologic activity or toxicity of the active agent. An adverse reaction also includes any undesirable or unexpected event requiring discontinuation of the active agent, modification of the dose, prolonged hospitalization, or the administration of supportive treatment.

"Affects" include an increase or decrease in degree, level, or intensity; a change in time of onset or duration; a change in type, kind, or effect, or a combination comprising at least one of the foregoing.

As used herein, "allelic variant" means one of the alternative forms at a genetic locus on a single chromosome. For loci in most of the human genome, a human has two chromosomes, which may carry the same or two different allelic variants.

"Adjusting administration of an active agent", "altering administration of an active agent", "adjusting dosing of an active agent", or "altering dosing of an active agent" are all equivalent and mean making no change in the dose or dosing regimen of the active agent; tapering off, reducing or increasing the dose of the active agent, ceasing to administer the active agent to the patient, or substituting a different active agent for the active agent.

"Dosing regimen" means the dose of an active agent taken at a first time by a patient and the interval (time or symptomatic) at which any subsequent doses of the active agent are taken by the patient. The additional doses of the active agent can be different from the dose taken at the first time.

A "dose" means the measured quantity of an active agent to be taken at one time by a patient.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "dosage form" means a unit of administration of an active agent. Examples of dosage forms include tablets, capsules, injections, suspensions, liquids, emulsions, creams, ointments, suppositories, inhalable forms, transdermal forms, and the like.

The term "effective amount" or "therapeutically effective amount" means an amount effective, when administered to a patient, to provide any therapeutic benefit. A therapeutic benefit may be an amelioration of symptoms, e.g., an amount effective to increase weight in AIDS patients with anorexia, cachexia, or significant weight loss. The amount that is "effective" will vary from subject to subject, depending on the age and general condition of the individual, the particular active agent, and the like. Thus, it is not always possible to specify an exact "effective amount." However, an appropriate "effective" amount in any individual case may be determined by one of ordinary skill in the art using routine experimentation. In certain circumstances a patient may not present symptoms of a condition for which the patient is being treated. A therapeutically effective amount of an active agent may also be an amount sufficient to provide a significant positive effect on any indicium of a disease, disorder, or condition, e.g. an amount sufficient to significantly increase body weight in AIDS patients with anorexia, cachexia, or significant weight loss. A significant effect on an indicium of a disease, disorder, or condition is statistically significant in a standard parametric test of statistical significance, for example Student's T-test, where $p<0.05$. An "effective amount or "therapeutically effective amount" of megestrol acetate may also be an amount of about 160 mg per day (40 mg q.i.d.) for breast cancer; about 320 mg per day or less, specifically about 40-320 mg per day in divided doses for endometrial carcinoma; or of any dosage amount approved by a governmental authority such as the US FDA, for use in treatment. In some embodiments "effective amount" or "therapeutically effective amount" of megestrol acetate may be an amount of about 800 mg megestrol acetate per day, specifically about 400-800 mg megestrol acetate per day of 40 mg megestrol acetate per unit dosage form of oral suspension, or 625 mg megestrol acetate per day of 125 mg megestrol acetate per unit dosage form of oral suspension, or of any dosage amount approved by a governmental authority such as the US FDA, for use in treatment.

"Efficacy" means the ability of an active agent administered to a patient to produce a therapeutic effect in the patient.

"Enhancing the safety profile" of an active agent means implementing actions or articles designed or intended to help reduce the incidence of adverse events associated with administration of the active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

"Informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

"Labeling" means all labels or other means of written, printed, graphic, electronic, verbal, or demonstrative communication that is upon a pharmaceutical product or a dosage form or accompanying such pharmaceutical product or dosage form.

A "medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, an enzyme "metabolizing" a substance means the substance is a substrate of the enzyme, i.e., the enzyme can chemically transform the substance.

A substance having a "narrow therapeutic index" (NTI) means a substance falling within any definition of narrow therapeutic index as promulgated by the U.S. Food and Drug Administration or any successor agency thereof, for example, a substance having a less than 2-fold difference in median lethal dose (LD50) and median effective dose (ED50) values or having a less than 2-fold difference in the minimum toxic concentration and minimum effective concentration in the blood; and for which safe and effective use of the substance requires careful titration and patient monitoring.

"Oral dosage form" includes a dosage form for oral administration. An oral dosage form can be a solid oral dosage form, for example, a tablet, and can comprise up to about 40 mg megestrol acetate. In one embodiment, a megestrol acetate solid dosage form comprises about 20 mg megestrol acetate, in another embodiment, a megestrol acetate solid dosage form comprises about 40 mg megestrol acetate. An oral dosage form can be a liquid oral dosage form, for example, an oral suspension. In one embodiment, a megestrol acetate oral suspension comprises about 40 mg/ml megestrol acetate, in another embodiment, a megestrol acetate oral suspension comprises about 125 mg/ml megestrol acetate. Amounts in dosage forms are given for megestrol acetate, however equivalent amounts of other forms of megestrol acetate can be used.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

A "pharmaceutical supplier" means a person (other than a medical care worker), business, charitable organization, governmental organization, or other entity involved in the transfer of active agent, including a dosage form thereof, between entities, for profit or not. Examples of pharmaceutical suppliers include pharmaceutical distributors, pharmaceutical wholesalers, pharmaceutical benefits managers, pharmacy chains, pharmacies (online or physical), hospitals, HMOs, supermarkets, the Veterans Administration, or foreign businesses or individuals importing active agent into the United States.

"Pharmacokinetic parameters" describe the in vivo characteristics of an active agent (or surrogate marker for the active agent) over time, such as plasma concentration (C), $C_{min}$, $C_{max}$, $C_n$, $C_{24}$, $T_{max}$, and AUC. "$C_{max}$" is the measured concentration of the active agent in the plasma at the point of maximum concentration. "$C_{min}$" is the measured concentration of the active agent in the plasma at the point of minimum concentration at steady state. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

"Pharmaceutically acceptable salts" include derivatives of the active agent (e.g., megestrol acetate), wherein the parent compound is modified by making acid or base addition salts thereof, and further refers to pharmaceutically acceptable solvates, including hydrates, of such compounds and such salts. Also included are all crystalline, amorphous, and polymorph forms. Examples of pharmaceutically acceptable salts include, but are not limited to, mineral or organic acid addition salts; and the like, and combinations comprising one or more of the foregoing salts. The pharmaceutically acceptable salts include salts, for example, from inorganic or organic acids. For example, acid salts include those derived from inorganic acids such as hydrochloric, hydrobromic, sulfuric, sulfamic, phosphoric, nitric and the like. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like.

"Phenotype" means an observable trait of an organism resulting from the interplay of environment and genetics. Examples include apparent rate of metabolism of substrates by a cytochrome p450 isozyme of an organism, such as the "poor metabolizer" (PM) or "ultrarapid metabolizer" (UM) phenotypes identified in humans for metabolism of substrates metabolized by CYP2D6.

"Polymorphism" means the differences in a DNA sequence that occur naturally among different individuals of a population. Single nucleotide substitutions, insertions, and deletions of nucleotides and repetitive sequences (microsatellites) are all examples of a polymorphism.

A "product" or "pharmaceutical product" means a dosage form of an active agent plus published material, and optionally packaging.

"Providing" means giving, administering, selling, distributing, transferring (for profit or not), manufacturing, compounding, or dispensing.

"Published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

"Product insert" means the professional labeling (prescribing information) for a pharmaceutical product, a patient package insert for the pharmaceutical product, or a medication guide for the pharmaceutical product.

"Professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

"Patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

"Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, "megestrol acetate therapy" refers to medical treatment of a symptom, disorder, or condition by administration of megestrol acetate.

"Risk" means the probability or chance of adverse reaction, injury, or other undesirable outcome arising from a medical treatment. An "acceptable risk" means a measure of the risk of harm, injury, or disease arising from a medical treatment that will be tolerated by an individual or group.

Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

"Safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

A "sensitive plasma concentration profile active agent" means an active agent for which a moderate change in plasma concentration can have a deleterious effect on the prescribed therapeutic intent. "Side effect" means a secondary effect resulting from taking an active agent. The secondary effect can be a negative (unfavorable) effect or a positive (favorable) effect.

A "substance" taken or administered with megestrol acetate means a substance that affects the safety, bioavailability, plasma concentration, efficacy, or a combination comprising at least one of the foregoing of megestrol acetate or the substance. A "substance" can be an active agent, an herbal supplement, a nutritional supplement, a vitamin, a xenobiotic, or an environmental contaminant.

A substance is a "substrate" of enzyme activity when it can be chemically transformed by action of the enzyme on the substance. "Enzyme activity" refers broadly to the specific activity of the enzyme (i.e., the rate at which the enzyme transforms a substrate per mg or mole of enzyme) as well as the metabolic effect of such transformations. Thus, a substance is an "inhibitor" of enzyme activity when the specific activity or the metabolic effect of the specific activity of the enzyme can be decreased by the presence of the substance, without reference to the precise mechanism of such decrease. For example a substance can be an inhibitor of enzyme activity by competitive, non-competitive, allosteric or other type of enzyme inhibition, by decreasing expression of the enzyme, or other direct or indirect mechanisms.

Similarly, a substance is an "inducer" of enzyme activity when the specific activity or the metabolic effect of the specific activity of the enzyme can be increased by the presence of the substance, without reference to the precise mechanism of such increase. For example a substance can be an inducer of enzyme activity by increasing reaction rate, by increasing expression of the enzyme, by allosteric activation or other direct or indirect mechanisms.

Any of these effects on enzyme activity can occur at a given concentration of active agent in a single sample, donor, or patient without regard to clinical significance. It is possible for a substance to be a substrate, inhibitor, or inducer of an enzyme activity. For example, the substance can be an inhibitor of enzyme activity by one mechanism and an inducer of enzyme activity by another mechanism. The function (substrate, inhibitor, or inducer) of the substance with respect to activity of an enzyme can depend on environmental conditions.

A "strongly significant" result from an in vitro study means a result which is a strong indicator of a potential in vivo interaction between an active agent and another co-administered substance. In vivo evaluation of the potential interaction between the active agent and another co-administered substance can be warranted to determine whether the interaction is sufficiently large to necessitate a dosage adjustment of one or both substances, or whether the interaction would require additional therapeutic monitoring.

For an in vitro study, a strongly significant level of observed induction by the active agent of a cytochrome p450 isozyme means induction that is at least 40% of the change in induction observed for a positive control inducer of the cytochrome p450 isozyme or at least a two-fold induction of the cytochrome p450 isozyme. Specifically, for a study using cultured primary hepatocytes, this level of induction is obtained in samples from a majority of the donors tested. More specifically, this level of induction is obtained using a concentration of the active agent in the range of plasma concentrations observed in vivo after administration of the active agent or the level of observed induction shows a concentration dependent trend in the samples of each donor showing at least 40% of the change in induction observed for a positive control inducer or at least a two-fold induction of the cytochrome p450 isozyme.

Additionally, for an in vitro study, a strongly significant level of observed inhibition of a cytochrome p450 isozyme by the active agent means that the active agent reduced the activity of the enzyme by 50% or more. Specifically, reduction in activity is observed to occur in a dose dependent way to produce this level of inhibition. More specifically, this level of reduction is obtained at a concentration of the active agent in the range of plasma concentrations observed in vivo after administration of the active agent. Yet more specifically, when primary cultures of hepatocytes are used in the enzyme activity assay, the level of reduction is observed in the samples from a majority of the donors tested.

"Subtherapeutic outcome" means a response to an active agent that is less than that anticipated from a dosing regimen of the active agent used for treatment of disease or for modification of physiological function.

The terms "treating" and "treatment" mean implementation of therapy with the intention of reducing in severity or frequency symptoms, elimination of symptoms or underlying cause, prevention of the occurrence of symptoms or their underlying cause, and improvement or remediation of damage.

A "user" means a patient, a medical care worker, or a pharmaceutical supplier.

The cytochrome p450 enzymes are a highly diverse superfamily of enzymes. Each cytochrome p450 enzyme is termed an "isoform" or "isozyme" since each derives from a different gene. Cytochrome p450 enzymes are categorized into families and subfamilies by amino acid sequence similarities. These enzymes are designated by the letters "CYP" followed by an Arabic numeral representing the family, a letter representing the sub-family, and another Arabic numeral representing a specific gene (e.g., CYP2D6). Particular isozymes discussed herein are named as per the recommendations of the P450 Gene Superfamily Nomenclature Committee (see e.g., "P450 superfamily: Update on new sequences, gene mapping, accession numbers, and nomenclature" Pharmacogenetics 6, 1-42 1996, part A pp. 1-21). Herein, the designation for a cytochrome p450 isozyme may encompass the homolog from any species identified as having such an isozyme. For example, CYP1A2 genes are known in at least rat, human, rabbit, hamster, dog, guinea pig, mouse, and chicken and the designation "CYP1A2" includes the CYP1A2 protein from any species known to have a CYP1A2 gene. In some embodiments, the designation for a cytochrome p450 isozyme is the human isozyme.

In one embodiment, CYP1A2 is human CYP1A2 (Entrez Gene ID: 1544; reference protein sequence Genbank NP_000752), and includes any allelic variants. Specifically, CYP includes any allelic variants included in the list of human CYP allelic variants maintained by the Human Cytochrome P450 (CYP) Allele Nomenclature Committee; more specifically it includes any of the *1 through *16 alleles. Additional reference amino acid sequences for human CYP1A2 include Genbank AAK25728, AAY26399, AAA35738, AAA52163, AAA52163, AAF13599, AAH67424, AAH67425, AAH67426, AAH67427, AAH67428, AAH67429, AAA52154, AAA52146, CAA77335, P05177, Q6NWU3, Q6NWU5, Q9BXX7, and Q9UK49.

In one embodiment, CYP2A6 is human CYP2A6 (Entrez Gene ID: 1548; reference protein sequence Genbank NP_000753), and includes any CYP2A6 allelic variants. Specifically, CYP2A6 includes any allelic variants included in the list of human CYP2A6 allelic variants maintained by the Human Cytochrome P450 (CYP) Allele Nomenclature Committee; more specifically it includes any of the *1 through *22 alleles. Additional reference amino acid sequences for human CYP2A6 include Genbank AAG45229, AAB40518, AAF13600, AAH96253, AAH96254, AAH96255, AAH96256, AAA52067, CAA32097, CAA32117, P11509, Q13120, and Q4VAU0.

In one embodiment, CYP2B6 is human CYP2B6 (Entrez Gene ID: 1555; reference protein sequence Genbank NP_000758), and includes any CYP2B6 allelic variants. Specifically, CYP2B6 includes any allelic variants included in the list of human CYP2B6 allelic variants maintained by the Human Cytochrome P450 (CYP) Allele Nomenclature Committee; more specifically it includes any of the *1 through *25 alleles. Additional reference amino acid sequences for human CYP2B6 include Genbank AAF32444, AAD25924, ABB84469, AAF13602, AAH67430, AAH67431, AAA52144, P20813, Q6NWU1, Q6NWU2, and Q9UNX8.

In one embodiment, CYP2C8 is human CYP2C8 (Entrez Gene ID: 1558; reference protein sequence Genbank NP_110518), and includes any CYP2C8 allelic variants. Specifically, CYP2B8 includes any allelic variants included in the list of human CYP2C8 allelic variants maintained by the Human Cytochrome P450 (CYP) Allele Nomenclature Committee; more specifically it includes any of the *1 through *10 alleles. Additional reference amino acid sequences for human CYP2C8 include Genbank CAH71307, AAR89907, CAA38578, AAH20596, AAA35739, AAA35740, AAA52160, AAA52161, CAA35915, CAA68550, P10632, Q5VX93, Q8WWB1, and Q9UCZ9.

In one embodiment, CYP2C9 is human CYP2C9 (Entrez Gene ID: 1559; reference protein sequence Genbank NP_000762), and includes any CYP2C9 allelic variants. Specifically, CYP2C9 includes any allelic variants included in the list of human CYP2C9 allelic variants maintained by the Human Cytochrome P450 (CYP) Allele Nomenclature Committee; more specifically it includes any of the *1 through *24 alleles. Additional reference amino acid sequences for human CYP2C9 include Genbank CAH71303, AAP88931, AAT94065, AAW83816, AAD13466, AAD13467, AAH20754, AAH70317, BAA00123, AAA52159, AAB23864, P11712, Q5EDC5, Q5VX92, Q61RV8, Q8WW80, Q9UEH3, and Q9UQ59.

In one embodiment, CYP2C19 is human CYP2C19 (Entrez Gene ID: 1557; reference protein sequence Genbank NP_000760), and includes any CYP2C19 allelic variants. Specifically, CYP2C19 includes any allelic variants included in the list of human CYP2C19 allelic variants maintained by the Human Cytochrome P450 (CYP) Allele Nomenclature Committee; more specifically it includes any of the *1 through *21 alleles. Additional reference amino acid sequences for human CYP2C19 include Genbank BAD02827, CAH73444, CAH74068, AAV41877, AAL31347, AAL31348, AAA36660, AAB59426, CAA46778, P33261, Q16743, Q767A3, Q8WZB1, and Q8WZB2.

In one embodiment, CYP2D6 is human CYP2D6 (Entrez Gene ID: 1565; reference protein sequence Genbank NP_000097), and includes any CYP2D6 allelic variants. Specifically, CYP2D6 includes any allelic variants included in the list of human CYP2D6 allelic variants maintained by the Human Cytochrome P450 (CYP) Allele Nomenclature Committee; more specifically it includes any of the *1 through *58 alleles. Additional reference amino acid sequences for human CYP2D6 include Genbank AAS55001, ABB01370, ABB01371, ABB01372, ABB01373, AAA35737, AAA53500, BAD92729, AAU87043, AAH66877, AAH67432, AAH75023, AAH75024, AAI06758, AAI06759, CAG30316, AAA52153, AAA36403, CAA30807, and P10635.

In one embodiment, CYP2E1 is human CYP2E1 (Entrez Gene ID: 1571; reference protein sequence Genbank NP_000764), and includes any CYP2E1 allelic variants. Specifically, CYP2E1 includes any allelic variants included in the list of human CYP2E1 allelic variants maintained by the Human Cytochrome P450 (CYP) Allele Nomenclature Committee; more specifically it includes any of the *1 through *7 alleles. Additional reference amino acid sequences for human CYP2E1 include Genbank CAH70047, BAA00902, BAA08796, AAA52155, AAD13753, AAF13601, CAI47002, AAH67433, AAH67435, AAZ77710, AAA35743, AAD14267, P05181, Q16868, Q5VZD5, Q6LER5, Q6NWT7, and Q6NWT9.

In one embodiment, CYP3A4 is human CYP3A4 (Entrez Gene ID: 1576; reference protein sequence Genbank NP_059488), and includes any CYP3A4 allelic variants. Specifically, CYP3A4 includes any allelic variants included in the list of human CYP3A4 allelic variants maintained by the Human Cytochrome P450 (CYP) Allele Nomenclature Committee; more specifically it includes any of the *1 through *20 alleles. Additional reference amino acid sequences for human CYP3A4 include Genbank AAF21034, AAG32290, AAG53948, EAL23866, AAF13598, CAD91343, CAD91645, CAD91345, AAH69418, AAI01632, BAA00001, AAA35747, AAA35742, AAA35744, AAA35745, CAA30944, P05184, P08684, Q6GRK0, Q7Z448, Q86SK2, Q86SK3, and Q9BZM0.

Various laboratory methods are known, including ones that are commercially available, for detecting the presence of allelic variants of cytochrome p450 isozymes in an individual or determining the metabolizer phenotype of an individual for a particular cytochrome p450 isozyme. Any suitable method known in the art may be used. Methods include analyzing a blood sample from the individual to determine the allelic variant of a particular cytochrome p450 isozyme gene present in the individual (for example by genotyping or haplotyping DNA or RNA from the gene using mass spectrometry, gel electrophoresis, or TAQMAN assays; or analyzing the protein sequence expressed by the gene). The metabolizer phenotype of the individual can be inferred based on the known properties of the allelic variants determined to be present in the individual. Alternatively, the blood sample can be used to measure enzyme activity of the cytochrome p450 isozyme using a suitable assay and isozyme-selective substrate. Among suitable isozyme-selective substrates are those used in the studies herein, or those suggested in publications of the United States Food and Drug Administration (FDA) directed to collecting cytochrome p450 isozyme data for regulatory submissions relating to an active agent, for example, the document "Drug Interaction Studies—Study Design, Data Analysis, and Implications For Dosing and Labeling; Preliminary Concept Paper", dated Oct. 1, 2004, and available from the "Genomics at FDA" regulatory information page of the FDA website.

The ability of megestrol acetate to act as a substrate of various cytochrome p450 isozymes was determined in studies described in the Examples.

The invention provides methods of using megestrol acetate. These methods include using megestrol acetate in the treatment or prevention of various diseases or conditions in a patient, including for example, advanced carcinoma of the breast or endometrium, endometriosis, menstrual disorders, or sex steroid dependent cancers. These methods also include using megestrol acetate in the treatment of diseases or conditions in an AIDS patient, including for example, anorexia, cachexia, or an unexplained, significant weight loss. Additionally, these methods include using megestrol acetate together with ethynyl estradiol as an oral contraceptive and for administration to subjects after castration. Using megestrol acetate in the treatment or prevention of a disease or condition in a patient can include administering megestrol acetate to a patient, dispensing megestrol acetate to a patient, or dispensing megestrol acetate to a medical care worker for administering to a patient.

In an embodiment, the method comprises informing a user that megestrol acetate is metabolized by cytochrome p450 isozymes. In one embodiment, the method comprises informing a user that megestrol acetate is metabolized by cytochrome p450 3A4. In some embodiments the cytochrome p450 isozyme is a human enzyme. The method can further comprise providing the user with megestrol acetate. If the user is a patient, the method can further comprise dosing the patient to improve safety or efficacy of megestrol acetate such that the dosing minimizes adverse events or side effects of megestrol acetate, specifically when megestrol acetate is administered to the patient with another substance, such as another active agent.

Informing the user that megestrol acetate is metabolized by a cytochrome p450 isozyme includes providing a user with information about megestrol acetate metabolism and any effect of an inducer or inhibitor of the cytochrome p450 isozyme on megestrol acetate metabolism as disclosed herein. Informing the user that megestrol acetate affects a cytochrome p450 isozyme includes informing a user of any of the following: that megestrol acetate is metabolized by cytochrome p450 isozyme, CYP3A4; that there is a potential active agent interaction between megestrol acetate and a substance that is a known inhibitor or inducer of CYP3A4; that caution is recommended when megestrol acetate and a known inhibitor or inducer of CYP3A4 are administered to a patient having a poor metabolizer phenotype for or reduced activity of CYP3A4; that the allelic variants of CYP3A4 present in the patient can further affect a potential active agent interaction between megestrol acetate and a substance that is an inducer or inhibitor of CYP3A4; that an inhibitor of CYP3A4 can decrease metabolism of megestrol acetate resulting in increased megestrol acetate plasma concentrations; that an inducer of CYP3A4 can increase metabolism of megestrol acetate resulting in decreased megestrol acetate plasma concentrations.

The method can further comprise informing the user that administration of megestrol acetate with a substance can affect the plasma concentration, bioavailability, safety, efficacy, or a combination comprising at least one of the foregoing of megestrol acetate or the substance. In some embodiments, the substance is an active agent; in some embodiments, the method further comprises providing the user with megestrol acetate or the substance.

In those embodiments wherein the substance is an inducer or inhibitor of a cytochrome p450 isozyme, informing the user that administration of megestrol acetate with a substance can affect the plasma concentration, bioavailability, safety, efficacy, or a combination comprising at least one of the foregoing of megestrol acetate includes providing a user with information about any effect on megestrol acetate plasma concentration, bioavailability, safety, efficacy, or a combination comprising at least one of the foregoing when the substance is administered with megestrol acetate. This includes informing a user of any of the following: that taking megestrol acetate with a substance can affect the bioavailability, safety, or efficacy of megestrol acetate; that administration of megestrol acetate and a substance that is an inhibitor or inducer of cytochrome p450 3A4 can affect plasma concentration, bioavailability, safety, efficacy, or a combination comprising at least one of the foregoing of megestrol acetate or the substance; that administering megestrol acetate and a substance that is an inhibitor of cytochrome p450 3A4 can result in decreased megestrol acetate metabolism resulting in increased plasma concentrations of megestrol acetate; that administering megestrol acetate and a substance that is an inducer of cytochrome p450 3A4 can result in increased megestrol acetate metabolism resulting in decreased plasma concentrations of megestrol acetate; or that caution is recommended when administering megestrol acetate with the substance, wherein the substance is an active agent that has a sensitive plasma concentration profile or a narrow therapeutic index.

The effect of administration of megestrol acetate with the substance can be determined by comparison of the plasma concentration, bioavailability, safety, efficacy, or a combination comprising at least one of the foregoing of the substance with and without administration of megestrol acetate or by comparison of the plasma concentration, bioavailability, safety, efficacy, or a combination comprising at least one of the foregoing of megestrol acetate with and without administration of the substance.

In some embodiments, the method of using megestrol acetate can further comprise administering megestrol acetate or a substance. Administration may be to a patient by the patient, a medical care worker, or other user. Megestrol acetate can be administered in a therapeutically effective amount. The substance can be an active agent. The active agent can have a sensitive plasma concentration profile or a narrow therapeutic index. In some embodiments, the method can further comprise informing the user that caution is recommended when administering megestrol acetate with a substance which is an active agent having a sensitive plasma concentration profile or a narrow therapeutic index. The method can also comprise monitoring a patient, for example monitoring the patient for an adverse reaction, a side effect, a subtherapeutic outcome, or a symptom of an active agent interaction or monitoring a patient's plasma concentration of megestrol acetate or the substance. The method can also comprise adjusting administration or dosing of the substance or megestrol acetate for the patient based on the monitoring, for example based on the determined plasma concentration of the substance or megestrol acetate.

In all of the embodiments herein, a medical care worker can determine the plasma concentration of a substance such as an active agent, including megestrol acetate, by performing or ordering the performance of any suitable method. For example, the medical care worker could order a test using blood drawn from the patient for determining the plasma concentration of megestrol acetate or the active agent.

Medical information provided in any of the methods described herein concerning the effects of administering megestrol acetate with an additional substance may alternatively be provided in layman's terms, so as to be better understood by patients or non-medical professionals. Those of skill in the medical art are familiar with the various layman's terms that can be used to describe the effects of active agent interactions.

In yet another embodiment, the method of using megestrol acetate comprises obtaining megestrol acetate from a container associated with published material providing information that megestrol acetate is metabolized by a cytochrome p450 isozyme, specifically CYP3A4. Information can also be provided that administering megestrol acetate with a substance that is an inducer or inhibitor of a cytochrome p450 isozyme can affect plasma concentration, bioavailability, safety, efficacy, or a combination comprising at least one of the foregoing of megestrol acetate or the substance. The information provided by the published material can comprise any combination of any information disclosed herein concerning megestrol acetate metabolism by a cytochrome p450 isozyme or any information disclosed herein concerning the effects of administering megestrol acetate with a substance on the plasma concentration, bioavailability, safety, efficacy, or a combination comprising at least one of the foregoing of the substance or megestrol acetate. The method can also comprise providing megestrol acetate in the container providing such information. The method can further comprise ingesting the megestrol acetate or the substance.

In an embodiment, the method comprises determining for a patient to whom megestrol acetate is going to be administered or is being administered whether a substance that is currently being or will be administered to the patient is an inhibitor or an inducer of CYP3A4; and determining risk for the patient of an adverse event during coadministration of megestrol acetate and the substance resulting from inhibition or induction of megestrol acetate metabolism by CYP3A4.

Depending on the determined risk of an adverse event, such as an active agent-related toxicity, the methods can further comprise administering megestrol acetate or the substance to the patient. For example, if there is no risk of an adverse event, or if the risk is determined to be acceptable, megestrol acetate and the substance can be administered to the patient. Alternatively, if there is a risk of an adverse event, or if the risk is determined to be unacceptable, either megestrol acetate can be administered to the patient but not the substance, or the substance can be administered to the patient but not megestrol acetate.

The method can further comprise determining that the patient has a poor metabolizer phenotype for CYP3A4 or determining that the patient belongs to an ethnic group in which there is a high frequency of a poor metabolizer phenotype, e.g. for CYP2B6, determining that the patient belongs to a Caucasian ethnic group.

Determining risk of an adverse reaction, such as a toxicity, resulting from coadministration of megestrol acetate and a substance is based on an appropriate set of risk parameters. As will be evident to those of skill in the art, the risk parameters to be considered will be based upon factors which influence the risk that a known or suspected adverse reaction will occur if the patient receives megestrol acetate with or without the substance, and will vary depending upon the substance in question for coadministration with lidocaine. Factors that may define the relevant risk parameters include effect of the substance or megestrol acetate on activity of relevant cytochrome p450 isozyme(s), i.e., CYP1A2, CYP2A6, CYP2B6, CYP2C8, CYP2C9, CYP2C19, CYP2D6, CYP2E1, or CYP3A4; the likelihood that certain preexisting conditions may exist in the patient; information collected from the patient including information relating to the patient's conduct; the patient's past or ongoing medical treatment, such as other procedures or medication which the patient may have received or is still receiving; results of certain diagnostic tests which have been performed; and the like. For example, if the substance is theophylline, risk factors identified as reducing theophylline clearance include the age of the patient, whether or not the patient is a smoker, and whether the patient has any of the following concurrent diseases or conditions: acute pulmonary edema, congestive heart failure, cor-pulmonale, fever, hypothyroidism, liver disease (e.g., cirrhosis or acute hepatitis), sepsis with multi-organ failure, and shock. Factors that should be considered before administering megestrol acetate include: age of the patient, whether the patient is pregnant or breast-feeding, other medicines taken by the patient (particularly anti-diabetic agents and insulin), and whether the patient has any of the following concurrent diseases or conditions: allergies, allergic reactions, diabetes mellitus; kidney disease, or liver disease. Also, the glucocorticoid activity of megestrol acetate oral suspension has not been fully evaluated. Clinical cases of new onset diabetes mellitus, exacerbation of pre-existing diabetes mellitus, and overt Cushing's Syndrome have been reported in association with the chronic use of megestrol acetate. In addition, clinical cases of adrenal insufficiency have been observed in patients receiving or being withdrawn from chronic megestrol acetate therapy in the stressed and non-stressed state. Furthermore, adrenocorticotropin (ACTH) stimulation testing has revealed the frequent occurrence of asymptomatic pituitary-adrenal suppression in patients treated with chronic megestrol acetate therapy. Therefore, the possibility of adrenal insufficiency should be considered in any patient receiving or being withdrawn from chronic megestrol acetate therapy who presents with symptoms and/or signs suggestive of hypoadrenalism (e.g., hypotension, nausea, vomiting, dizziness, or weakness) in either the stressed or non-stressed state. Laboratory evaluation for adrenal insufficiency and consideration of replacement or stress doses of a rapidly acting glucocorticoid are strongly recommended in such patients. Failure to recognize inhibition of the hypothalamic-pituitary-adrenal axis may result in death. Finally, in patients who are receiving or being withdrawn from chronic megestrol acetate therapy, consideration should be given to the use of empiric therapy with stress doses of a rapidly acting glucocorticoid during stress or serious intercurrent illness (e.g., surgery, infection)

Information collected from the patient for determining risk may be obtained prior to the initial dispensation of megestrol acetate or the substance to the patient or may be obtained from the patient on a periodic basis. For example, after treatment with megestrol acetate and the substance is begun, information on the onset of certain symptoms, which may be indicative of the need for changes in the patient's treatment regimen, may be obtained from the patient on a periodic basis. For example if theophylline and a substance that interferes with theophylline clearance are coadministered, information on development of nausea or vomiting, particularly repetitive vomiting, or other signs or symptoms consistent with theophylline toxicity should be obtained.

Determining risk can comprise accessing a computer-hosted database to obtain information relevant to assessing risk, for example adverse reactions associated with an active agent, active agent interactions, risk factors for an adverse reaction in administration of an active agent, dosing, and the like. The database may be in the form of a look-up table, or similar structure, that provides output information based on the input of information.

Alternatively, determining risk can comprise obtaining information relevant to assessing risk from standard treatment guidelines, textbooks, compendial literature, journals, drug manufacturer guidelines, internet websites providing information on active agent interactions (e.g., "Drug Interaction Checker" at the MEDScape website or the drug interaction website maintained by Dr. D. Flockhart, Indiana University School of Medicine); or FDA requirements for particular active agents.

Diagnostic tests may be probative of the concentration of one or more active agents, including a prescribed active agent, to assure that appropriate dosing is maintained in the patient. Such diagnostic testing may be conducted on any bodily fluid or waste product of the patient, including the blood, serum, plasma, saliva, semen or urine, as well as the feces. Diagnostic testing may also be performed on a biopsy of any tissue of the patient or may include genetic testing, which may be indicative of a genetic predisposition to a particular adverse side effect. Other forms of diagnostic testing, such as diagnostic imaging, or tests which may be probative of the proper functioning of any tissue, organ, or system, are also contemplated. Preferably, appropriate information or diagnostic test results are obtained and considered in determining risk.

In an embodiment, the method comprises administering megestrol acetate to a patient. Monitoring the patient during administration of megestrol acetate if the patient is taking a substance that is a known inhibitor or a known inducer of cytochrome p450 3A4 can be performed. Adjusting administration of megestrol acetate or the substance to the patient to avoid an adverse event in the patient can be performed. Determining that a substance that is an inducer or an inhibitor of cytochrome p450 3A4 is administered to the patient can be included in the method.

Such methods can include informing a patient receiving a substance or the patient's medical care worker that megestrol acetate is a substrate of CYP3A4; and adjusting administration of megestrol acetate or the substance to the patient as a result of the informing to avoid an adverse event in the patient.

In an embodiment, the method comprises informing a patient receiving an active agent or the patient's medical care worker that megestrol acetate is a substrate of a cytochrome P450 isozyme; and adjusting administration of megestrol acetate or the active agent to the patient as a result of the informing to avoid an adverse event or a subtherapeutic outcome in the patient. The active agent is a known inhibitor or inducer of the cytochrome P450 isozyme.

In an embodiment, the method comprises informing a patient receiving an active agent or the patient's medical care worker that megestrol acetate is a substrate of a cytochrome P450 isozyme and adjusting administration of megestrol acetate or the active agent to the patient as a result of the informing to produce a treatment response in the patient. The active agent is a known inhibitor or inducer of the cytochrome P450 isozyme.

In an embodiment, the method comprises administering megestrol acetate to a patient; and monitoring the patient during administration of megestrol acetate if the patient is taking a substance that is a known inhibitor, or inducer of activity of a cytochrome P450 isozyme. The cytochrome P450 can be CYP3A4.

In an embodiment, the method comprises determining that a substance that is a known inhibitor, or inducer of activity of a cytochrome P450 isozyme is administered to the patient; and adjusting administration of megestrol acetate or the substance to the patient to avoid an adverse reaction or a subtherapeutic outcome. The cytochrome P450 can be CYP3A4.

In an embodiment, the method comprises determining that megestrol acetate is a substrate of a cytochrome P450 isozyme; administering megestrol acetate to a patient; and monitoring the patient during administration of megestrol acetate if a substance that is a known inhibitor, or inducer of activity of the cytochrome P450 isozyme is coadministered to the patient. The cytochrome P450 can be CYP3A4.

Such methods can include informing a user that megestrol acetate is a substrate of a cytochrome P450 isozyme. The method can include informing the user that administration of megestrol acetate with a substance can affect the plasma concentration, bioavailability, safety, efficacy, or a combination comprising at least one of the foregoing of megestrol acetate or the substance. The method can include informing the user of any information disclosed herein about megestrol acetate metabolism and any information disclosed herein about the effect of megestrol acetate or the substance on the plasma concentration, bioavailability, safety, efficacy, or a combination comprising at least one of the foregoing of megestrol acetate or the substance when megestrol acetate is used with the substance.

Determining that a substance that is a known inhibitor, or inducer of CYP3A4 is administered to a patient in need of megestrol acetate therapy can be performed by consulting with the patient, a medical care worker administering medications to the patient, a prescription database including medications prescribed to the patient, or by any other method known in the art.

Determining that megestrol acetate is a substrate of cytochrome P450 3A4 or determining that co-administration of megestrol acetate and a substance that inhibits CYP3A4 may result in an increased megestrol acetate plasma concentration, or that co-administration of megestrol acetate and a substance that induces CYP3A4 may result in a decreased megestrol acetate plasma concentration can be performed by consulting the package insert for the megestrol acetate product administered to the patient, consulting a database including prescribing information and potential risks for megestrol acetate, or by any other method known in the art.

Monitoring the patient can comprise monitoring the patient's plasma concentration of megestrol acetate or the substance; monitoring the patient for symptoms of an active agent interaction between the substance and megestrol acetate; monitoring the patient for an adverse reaction (e.g., toxicity or a subtherapeutic outcome) resulting from administration of the substance and megestrol acetate; monitoring the patient for an adverse reaction (e.g., toxicity or a subtherapeutic outcome) associated with megestrol acetate; or monitoring the patient for decreased efficacy of megestrol acetate.

Monitoring the patient can be monitoring any appropriate patient-specific, disease-specific, or substance-specific parameter appropriate to avoid or safely manage an active agent interaction. Monitoring the patient can be, for example, monitoring the patient for an adverse reaction, a subtherapeutic outcome, a side effect, or a symptom of an active agent interaction, for example by physical examination or visual identification; monitoring the blood level of megestrol acetate or the substance in the patient; monitoring clinical laboratory tests appropriate for megestrol acetate, the substance, or a medical diagnosis for the patient; monitoring therapeutic effect of megestrol acetate or the substance on the patient's condition; monitoring occurrence in the patient of a known side effect, subtherapeutic outcome, or adverse reaction of megestrol acetate or the substance; monitoring the patient for occurrence of an unexpected response during treatment; monitoring changes in control, signs, or symptoms of a condition of the patient, or determining a complete list of medical diagnoses for the patient. To monitor a patient for an adverse reaction, sub-therapeutic outcome, or a side effect, a doctor may order blood or urine tests, including but not limited to blood samples for white blood count, liver function tests, blood chemistries, EKGs, blood urea nitrogen and creatinine. Any other tests known to those skilled in the art that would help determine or assess the presence of and/or extent or significance of an adverse event, adverse reaction, or side effect. Monitoring the patient can be performed by the patient or by a medical care worker.

Most active agents have a large list of non-severe or mild adverse side effects. These adverse side effects have widely variable incidence, according to individual sensitivity.

For megestrol acetate, the most frequently reported adverse reactions to megestrol acetate therapy in patients with breast cancer are weight gain, thromboebolic phenomena including thrombophlebitis and pulmonary embolism. Less frequently or rarely reported adverse reactions associated with megestrol acetate therapy include heart failure, nausea, vomiting, edema, breakthrough menstrual bleeding, dyspnea, hyperglycermia, glucose intolerance, alopecia, hypertension, carpal tunnel syndrome, mood changes, hot flashes, malaise, asthenia, lethargy, sweating and rash. Frequently reported adverse reactions to megestrol acetate therapy in AIDS patients with anorexia, cachexia, or an unexplained, significant weight loss are diarrhea, impotence, rash, flatulence, hypertension, asthenia, insomnia, nausea, anemia, fever, decreased libido, dyspepsia, hyperglycemia, headache, pain, vomiting, pneumonia, and urinary frequency.

Determining that a patient experiences an adverse reaction can be performed by obtaining information from the patient regarding onset of certain symptoms which may be indicative of the adverse reaction, results of diagnostic tests indicative of the adverse reaction, and the like.

Determining the level of metabolism of megestrol acetate in a subject may be performed for example by determining plasma concentrations of megestrol acetate or of an appropriate metabolite of megestrol acetate, or any other methods known in the art.

Adjusting administration of megestrol acetate or the substance to the patient to avoid an adverse reaction or a subtherapeutic outcome, or adjusting dosing regimens can be provided by one of ordinary skill in the art, taking into consideration such factors as the age, sex, and health of the patient, as well as active agents the patient may be taking at the time. Optionally, the patient can be monitored at the initial or a subsequent stage of treatment to ensure therapeutic plasma levels of megestrol acetate or the substance are achieved or maintained.

Methods of using megestrol acetate include methods in which the user is a patient and additionally can comprise administering megestrol acetate and an active agent to the patient. The patient may be, for example, a human patient, a patient in need of treatment of breast cancer or an AIDS patient with anorexia, cachexia, or an unexplained, significant weight loss, a patient in need of megestrol acetate therapy, a patient receiving prophylactic megestrol acetate treatment, or a patient undergoing megestrol acetate therapy. The amount of megestrol acetate administered may be a therapeutically effective amount.

In an embodiment, the method can additionally include monitoring the patient's plasma concentration of the active agent or megestrol acetate. When megestrol acetate is administered together with another active agent, methods of using megestrol acetateacetate can include determining the plasma concentration of the active agent or megestrol acetate and adjusting dosing of the active agent or megestrol acetate for the patient based on the determined plasma concentration of the active agent or megestrol acetate.

When the substance administered with megestrol acetate is an NTI or sensitive plasma concentration profile active agent, methods using a blood test to monitor plasma levels of the NTI or sensitive plasma concentration profile active agent comprise administering to a patient megestrol acetate and the NTI or sensitive plasma concentration profile active agent, and monitoring the blood levels of the NTI or sensitive plasma concentration profile active agent. Methods can also include adjusting dosing of the NTI or sensitive plasma concentration profile active agent for the patient based on the determined plasma concentration of the active agent.

In some embodiments, the NTI active agent comprises warfarin. Warfarin, 3-(a -acetonylbenzyl)-4-hydroxycoumarin, is an anticoagulant, which is eliminated by metabolism by cytochrome p450 isoforms including CYP2C9, CYP2C19, CYP2C8, CYP2C18, CYP1A2, and CYP3A4. Warfarin has a narrow therapeutic index such that too little can lead to excessive clotting, while excessive warfarin can lead to excessive bleeding. The dosing of warfarin is individualized according to the patient's sensitivity to the active agent as indicated, for example, by the Prothrombin Time/International Normalized Ratio (PT/INR). The PT/INR gives an indication of how fast blood is clotting. The recommended initial dose is 2-5 mg/day, with 2-10 mg/day as the maintenance dose. Warfarin tablets for oral administration include tablets comprising 1, 2, 2.5, 3, 4, 5, 6, 7.5, and 10 mg of warfarin. The INR may be adjusted to 2.0-4.5, or 2.0-3.0 or 2.5-3.5 depending on whether the warfarin is being administered to treat venous thromboembolism, non-valvular atrial fibrillation, post-myocardial infarction, heart valve prophylaxis, or recurrent systemic embolism.

In the PT test, a reagent which induces coagulation is added to a sample of the patient's plasma. The reagent typically primarily comprises thromboplastin and calcium chloride. Many commercially available PT reagents contain crude thromboplastin extracted from natural sources, e.g., rabbit brain, rabbit brain/lung mixtures, human placenta, or bovine brain, although recombinant thromboplastin may also be employed. Prothrombin time assays are performed by mixing the plasma sample and reagent at a constant temperature such as 37° C., and monitoring the progress of the reaction until a perceptible clot (or "gel clot") is detected. The development of a gel clot is the end point of the reaction. This end point may be detected in various ways such as by viscosity change, by electrode reaction, and, most commonly, by photometric means. The test result is generally compared to a result using a normal (control) plasma and converted to an INR.

The International Normalized Ratio, or INR, was developed to standardize PT values, so that test results from different thromboplastins and coagulation analyzers become equivalent. Under the INR system, a thromboplastin is assigned an International Sensitivity Index (ISI) value. The ISI indicates the relative sensitivity of the thromboplastin compared to an international reference thromboplastin. If a thromboplastin has the same sensitivity as the reference thromboplastin, then its ISI is 1.0. A higher ISI value indicates that a thromboplastin is less sensitive than the reference thromboplastin. The ISI is used in the following formula to calculate an INR value from a PT value: INR=(patient PT/mean normal PT)ISI. The ISI is usually determined by the thromboplastin manufacturer. Different ISI values are assigned for different models or classes of coagulation analyzers.

In an embodiment of the method of using megestrol acetateacetate in which the substance is warfarin, the method comprises administering to a patient megestrol acetate and warfarin, and monitoring the blood levels of warfarin and megestrol acetate or monitoring the Prothrombin Time/International Normalized Ratio.

In another embodiment, the method comprises administering megestrol acetate and warfarin to a patient in need of megestrol acetate and an anticoagulant, and monitoring the Prothrombin Time/International Normalized Ratio. Monitoring the Prothrombin Time/International Normalized Ratio may be performed daily, every other day, weekly, every other week, or monthly, for example. The method may further comprise providing to the patient or medical care worker instructions regarding measuring the Prothrombin Time/International Normalized Ratio daily, every other day, weekly, every other week, monthly, or according to another schedule or time criteria.

The NTI active agent can also comprise phenyloin. Phenyloin, 5,5-diphenylhydantoin, is an antiepileptic active agent useful in the treatment of epilepsy which is eliminated by metabolism by cytochrome P450 isoforms including CYP1A2, CYP2C9, CYP2C19, and CYP3A4. Phenyloin has a narrow therapeutic index such that too little can lead to insufficient results and excessive phenyloin can lead to phenyloin toxicity. The typical clinically effective serum level is about 10 to about 20 mg/mL. The recommended initial dose is one 100 mg capsule 3 to 4 times per day, with 300 mg/day dose in three divided doses or one single dose per day. The dosing of phenyloin can be individualized according to the patient's sensitivity to the active agent by measuring plasma concentration of phenyloin.

In an embodiment of the method of using megestrol acetate, in which the substance is phenyloin, the method comprises administering megestrol acetate and phenyloin to a patient in need of megestrol acetate and an antiepileptic, and monitoring the blood levels of phenyloin.

Also disclosed herein are methods of manufacturing a megestrol acetate pharmaceutical product.

In one embodiment, the method comprises packaging a megestrol acetate dosage form with published material providing information of megestrol acetate metabolism by a cytochrome p450 isozyme. The information can include any information disclosed herein concerning megestrol acetate metabolism by a cytochrome p450 isozyme. The information can also include any information disclosed herein about the effects of administering megestrol acetate and a substance on the plasma concentration, bioavailability, safety, efficacy, or a combination comprising at least one of the foregoing of megestrol acetate or the substance when the substance is used with megestrol acetate.

The invention provides articles of manufacture.

In some embodiments, the article of manufacture comprises a container containing a dosage form of megestrol acetate and optionally information or published material, e.g., as product inserts or product labels. The information or published material can indicate quantities of the components to be administered, guidelines for administration, safety issues, and the like.

In some embodiments, the container is associated with published material informing that megestrol acetate is metabolized by a cytochrome p450 isozyme. The information provided by the published material can include any information disclosed herein concerning megestrol acetate metabolism by a cytochrome p450 isozyme. The published material can also include any information disclosed herein concerning the effect of administering megestrol acetate and a substance on the plasma concentration, bioavailability, safety, efficacy, or a combination comprising at least one of the foregoing of megestrol acetate or the substance when the substance is used with megestrol acetate. The published material may be in the form of printed labeling, or in some other form.

Also disclosed herein is an article of manufacture comprising packaging material and a dosage form contained within the packaging material, wherein the dosage form comprises megestrol acetate, and wherein the packaging material comprises a label approved by a regulatory agency for the product. Examples of regulatory agencies are the US FDA or the European Agency for the Evaluation of Medicinal Products (EMEA). The label can inform of any information disclosed herein about the effect of megestrol acetate metabolism by a cytochrome p450 isozyme or any information disclosed herein about the effects of administering megestrol acetate and a substance on the plasma concentration, bioavailability, safety, efficacy, or a combination comprising at least one of the foregoing of megestrol acetate or the substance when the substance is used with megestrol acetate.

In one embodiment, the article of manufacture comprises a container holding a dosage form of megestrol acetate associated with published material informing that there is a potential active agent interaction with an active agent that has a narrow therapeutic index, or that administration of megestrol acetate with the active agent that has a narrow therapeutic index can affect the bioavailability, safety, efficacy, or a combination comprising at least one of the foregoing of the active agent that has a narrow therapeutic index. The published material may further comprise instructions to monitor the blood levels of the active agent that has a narrow therapeutic index.

In embodiments of the articles of manufacture, the dosage form will typically be contained in a suitable container capable of holding and dispensing the dosage form and which will not significantly interact with the active agent(s) in the dosage form. Further, the container will be in physical relation with the published material. The published material may be associated with the container by any means that maintains physical proximity of the two. By way of example, the container and the published material can both be contained in a packaging material such as a box or plastic shrink wrap. Alternatively, the published material can be bonded to the container, such as with glue that does not obscure the published material, or with other bonding or holding means. Yet another alternative is that the published material is placed within the container with the dosage form.

Someone can also hand the published material to the patient, for example a pharmacist can hand a product insert, patient package insert, or medication guide to a patient in conjunction with dispensing the dosage form. The published material may be a product insert, patient package insert, medication guide, flyer, brochure, or a packaging material for the dosage form such as a bag, or the like.

In any of the embodiments disclosed herein the published material or information associated with or provided by a container can be contained in any fixed and tangible medium. For example, the information can be part of a leaflet, brochure, or other printed material provided with a container or separate from a container. The information can also take the form of a flyer, advertisement, or the label for marketing the active agent approved by a regulatory agency. The information can also be recorded on a compact disk, DVD or any other recording or electronic medium.

The container can be in the form of bubble or blister pack cards, optionally arranged in a desired order for a particular dosing regimen. Suitable blister packs that can be arranged in a variety of configurations to accommodate a particular dosing regimen are well known in the art or easily ascertained by one of ordinary skill in the art.

Megestrol acetate dosage forms existing as liquids, solutions, emulsions, or suspensions can be packaged in a container for convenient dosing of pediatric or geriatric patients. For example, prefilled droppers (such as eye droppers or the like), prefilled syringes, and similar containers housing the liquid, solution, emulsion, or suspension form are contemplated.

Megestrol acetate can be formulated as a dosage form for administration where the formulation generally contains megestrol acetate and a pharmaceutically acceptable excipient. As used herein, "pharmaceutically acceptable excipient" means any other component added to the pharmaceutical formulation other than the active agent. Excipients may be added to facilitate manufacture, enhance stability, control release, enhance product characteristics, enhance bioavailability, enhance patient acceptability, etc. Pharmaceutical excipients include carriers, fillers, binders, disintegrants, lubricants, glidants, compression aids, colors, sweeteners, preservatives, suspending agents, dispersing agents, film formers, flavors, printing inks, buffer agents, pH adjusters, preservatives etc.

The substance used with megestrol acetate in the methods and articles of manufactures described herein may have certain effects, direct or indirect, on the activity of a cytochrome p450 enzyme. The substance can be a substrate, inhibitor, or inducer of a Phase I or Phase II metabolic enzyme; specifically, the substance is a substrate, inhibitor, or inducer of a cytochrome p450 isozyme. More specifically, the substance is an inhibitor or inducer of cytochrome p450 3A4, or is a substrate of cytochrome p450 3A4.

In any of the above methods or articles, the substance can be an active agent.

Examples of inhibitors of CYP1A2 include fluvoxamine, ciprofloxacin, cimetidine, amiodarone, fluoroquinolones (e.g., ciprofloxacin, gatifloxacin, levofloxacin, lomefloxacin, moxifloxacin, norfloxacin, or ofloxacin), furafylline, interferon, methoxsalen, and mibefradil. Examples of inducers of CYP1A2 include insulin, methylcholanthrene, modafinil, nafcillin, beta-naphthoflavone, omeprazole, and tobacco.

Examples of inhibitors of CYP2A6 include tranylcypromine, methoxsalen, pilocarpine, and tryptamine. Examples of inducers of CYP2A6 include dexamethasone and pyrazole.

Examples of inhibitors of CYP2B6 include thiotepa and ticlopidine. Examples of inducers of CYP2B6 include phenobarbital and rifampin.

Examples of inhibitors of CYP2C8 include quercetin, the glitazones, gemfibrozil, montelukast, and trimethoprim. Examples of inducers of CYP2C8 include rifampin.

Examples of inhibitors of CYP2C9 include amiodarone, fenofibrate, fluconazole, fluvastatin, fluvoxamine, isoniazid, lovastatin, phenylbutazone, probenicid, sertraline, sulfamethoxazole, sulfaphenazole, teniposide, voriconazole, and zafirlukast. Examples of inducers of CYP2C9 include rifampin and secobarbital.

Examples of inhibitors of CYP2C19 include chloramphenicol, cimetidine, felbamate, fluoxetine, fluvoxamine, indomethacin, ketoconazole, lansoprazole, modafinil, omeprazole, oxcarbazepine, probenicid, ticlopidine, and topiramate. Examples of inducers of CYP2C19 include carbamazepine, norethindrone, prednisone, and rifampin (rifampicin).

Examples of inhibitors of CYP2D6 include amiodarone, bupropion, celecoxib, chlorpromazine, chlorpheniramine, cimetidine, citalopram, clomipramine, cocaine, doxepin, doxorubicin, duloxetine, escitalopram, fluoxetine, halofantrine, red-haloperidol, levomepromazine, metoclopramide, methadone, mibefradil, midodrine, moclobemide, paroxetine, quinidine, ranitidine, ritonavir, sertraline, terbinafine, ticlopidine, histamine H1 receptor antagonists, diphenhydramine, chlorpheniramine, clemastine, perphenazine, hydroxyzine, and tripelennamine. Examples of inducers of CYP2D6 include rifampicin and dexamethasone.

Examples of inhibitors of CYP2E1 include diethyl-dithiocarbamate and disulfuram. Examples of inducers of CYP2E1 include ethanol and isoniazid.

Examples of inhibitors of CYP3A4 include HIV Antivirals: e.g., delavirdine, indinavir, nelfinavir, and ritonavir; amiodarone, aprepitant, cinchloramphenicol, cimetidine, clarithromycin, diethyl-dithiocarbamate, diltiazem, erythromycin, fluconazole, fluvoxamine, gestodene, grapefruit juice, Seville orange juice, imatinib, itraconazole, ketoconazole, mifepristone, nefazodone, norfloxacin, norfluoxetine, mibefradil, star fruit, verapamil, and voriconazole. Examples of inducers of CYP3A4 include HIV Antivirals: e.g., efavirenz, and nevirapine; barbiturates, carbamazepine, efavirenz, glucocorticoids, modafinil, nevirapine, phenobarbital, phenyloin, rifampin, St. John's wort, troglitazone, oxcarbazepine, pioglitazone, and rifabutin.

In any of the embodiments described herein, the substance can be a sensitive plasma concentration profile active agent. Examples of a sensitive plasma concentration profile active agent include cyclophosphamide, efavirenz, fosphenyloin, glimepiride, mexiletine, phenyloin, progesterone, tamoxifen, theophylline, warfarin, and any active agent having a narrow therapeutic index.

In any of the embodiments described herein, the substance can be an active agent having a narrow therapeutic index. Examples of narrow therapeutic index active agents include aprindine, carbamazepine, clindamycin, clonazepam, clonidine, cyclosporine, digitoxin, digoxin, disopyramide, ethinyl estradiol, ethosuximide, fosphenyloin, guanethidine, isoprenaline, lithium, methotrexate, phenobarbital, phenyloin, pimozide, prazosin, primidone, procainamide, quinidine, sulfonylurea compounds (e.g., acetohexamide, glibenclamide, gliclazide, glyclopyramide, tolazamide, tolbutamide), tacrolimus, theophylline compounds (e.g., aminophylline, choline theophylline, diprophylline, proxyphylline, and theophylline), thioridazine, valproic acid, warfarin, and zonisamide.

The invention is further illustrated by the following examples.

Example 1

Megestrol Acetate Metabolism by Cytochrome p450 Isozymes in Pooled Human Microsomes The study of this example was performed to determine the metabolism of megestrol acetate by specific CYP isozymes using pooled human liver microsomes and CYP isozyme-specific inhibitors. Human liver microsomes were incubated in the presence of megestrol acetate and in the presence or absence of cytochrome p450 (CYP) isozyme-specific inhibitors. CYP isozyme-specific inhibitors were prepared as 100× stock solutions in the solvent listed below, except for quercetin, a CYP2C8 inhibitor. Quercetin was prepared as a 1,000× stock solution in the solvent listed below. The final CYP isoform-specific inhibitor concentrations and solvents are shown in Table 2.

TABLE 2

CYP Isoform Specific Inhibitors

| CYP isoform | Specific CYP isozyme Inhibitor | Inhibitor concentration | Solvent |
|---|---|---|---|
| CYP1A2 | Furafylline* | 5 µM | acetonitrile |
| CYP2A6 | Tranylcypromine | 10 µM | water |
| CYP2B6 | Ticlopidine | 1 µM | methanol |
| CYP2C8 | Quercetin | 100 µM | DMSO |
| CYP2C9 | Sulfaphenazole | 1.5 µM | acetonitrile |
| CYP2C19 | Nootkatone | 80 µM | methanol |
| CYP2D6 | Quinidine | 2.0 µM | methanol |
| CYP2E1 | Diethyldithiocarbamate | 100 µM | water |
| CYP3A4 | Ketoconazole | 1 µM | acetonitrile |

*Furafylline is a mechanism based inhibitor and was pre-incubated with microsomes for 15 minutes prior to adding the megestrol acetate or a CYP isoform-selective substrate.

Megestrol acetate (molecular weight: 384.51 g/mol) stock solutions were prepared in acetonitrile at 100 times (100×) the final concentration. The stock solutions were added to incubation mixtures to obtain the final concentrations of 5 and 50 µM, each containing 1% acetonitrile.

Microsomes were prepared by differential centrifugation of liver homogenates pooled from at least ten human donors.

Incubation mixtures were prepared in 0.1 M Tris buffer (pH 7.4) and contained microsomes (0.5 mg protein/mL), an appropriate volume of inhibitor solvent or a CYP isoform-specific inhibitor, and megestrol acetate (5 and 50 µM). After a 5 minute preincubation, nicotinamide adenine dinucleotide phosphate (NADPH) regenerating system (NRS; 1.7 mg/mL β-NADP, 7.8 mg/mL glucose-6-phosphate, and 6 units/mL glucose-6-phosphate dehydrogenase in 2% sodium bicarbonate solution) was added to initiate the reaction. The final incubation volume was 0.5 mL. Incubations were continued for 60 minutes. For CYP1A2, incubation mixtures containing microsomes, 1% acetonitrile, and NSR in 0.1 M Tris buffer (pH 7.4) were preincubated for 15 minutes prior to adding megestrol acetate, furafylline or appropriate volume of inhibitor solvent to initiate reactions.

All incubations were conducted at 37±1° C. in a shaking water bath. All incubations were carried out in triplicates.

To verify that the CYP isoform-specific inhibitors and their concentrations chosen were suitable for evaluating the contributions of specific CYP isoforms towards the metabolism of megestrol acetate, metabolic positive controls were carried out. In metabolic positive controls, incubation mixtures were prepared in 0.1 M Tris buffer (pH 7.4) and contained microsomes (at 0.5 mg protein/mL), a CYP isoform-selective substrate and a CYP isoform-specific inhibitor. After a 5-minute pre-incubation, NRS was added to the incubation mixtures to initiate reactions. The final incubation volume was 0.5 mL. Incubations were continued for 60 minutes. As comparison, incubations containing microsomes (at 0.5 mg protein/mL) in 0.1 M Tris buffer (pH 7.4), a CYP isoform-selective substrate, and appropriate volume of inhibitor solvent were carried out under same conditions. In these experiments, each CYP isoform-selective substrate was prepared as 100× stock solutions in the solvent listed below. The final substrate concentrations, solvents, metabolite formed from each isoform-selective substrate, and metabolite assay methods are listed in Table 3.

TABLE 3

Isoform-selective substrates for cytochrome p450 isozymes.

| CYP isoform | Isoform-selective substrate | Substrate concentration | Solvent | Metabolite formed | Metabolite Assay |
|---|---|---|---|---|---|
| CYP1A2 | Phenacetin | 50 µM | ACN | acetaminophen | LC/MS |
| CYP2A6 | Coumarin | 8 µM | ACN | 7-hydroxycoumarin | HPLC-UV |
| CYP2B6 | Bupropion | 1 mM | ACN | Hydroxybupropion | LC/MS |
| CYP2C8 | Paclitaxel | 5 µM | ACN | 6-hydroxypaclitaxel | LC/MS |
| CYP2C9 | Tolbutamide | 150 µM | ACN | 4'-methylhydroxytolbutamide | LC/MS |
| CYP2C19 | S-Mephenytoin | 50 µM | ACN | 4'-hydroxymephenytoin | LC/MS |
| CYP2D6 | Dextromethorphan | 5 µM | Water | dextrorphan | LC/MS |
| CYP2E1 | Chlorzoxazone | 50 µM | ACN | 6-hydroxychlorzoxazone | LC/MS |
| CYP3A4 | Testosterone | 100 µM | ACN | 6β-hydroxytestosterone | HPLC-UV |

Matrix control samples were included to provide a source of background from matrix components. In the matrix controls, incubation mixtures were prepared in 0.1 M Tris buffer (pH 7.4) and contained microsomes (at 0.5 mg protein/mL), an appropriate volume of inhibitor solvent, and 1% acetonitrile. Reactions were initiated and carried out as described above. For CYP1A2, the matrix control was carried out by incubating microsomes, 1% acetonitrile, and NRS for 15 minutes prior to adding an appropriate volume of inhibitor solvent.

Metabolic negative controls were included to distinguish potential nonenzymatic metabolism from P450-mediated metabolism of megestrol acetate. For the metabolic negative controls, incubation mixtures were prepared in 0.1 M Tris buffer (pH 7.4) and contained microsomes (at 0.5 mg protein/mL), megestrol acetate (at each concentration) and a CYP isoform-specific inhibitor or an appropriate volume of inhibitor solvent. After a 5-minute preincubation, 2% sodium bicarbonate solution was added to the incubation mixtures. The final incubation volume was 0.5 mL. Incubations were continued for 60 minutes. Again, for the CYP1A2 metabolic negative control, mixtures containing microsomes, furafylline, and 2% sodium bicarbonate solution were incubated for 15 minutes prior to adding megestrol acetate.

Incubation reactions, including the matrix controls and metabolic negative controls, were terminated by adding 0.5 mL methanol.

Incubation reactions for positive controls were terminated by adding 0.5 mL methanol, except for paclitaxel (CYP2C8) which was terminated by adding 0.75 mL of acetonitrile.

After incubation reactions were terminated, the samples were transferred to cryovials and stored at −70±10° C. until analysis.

The metabolism of megestrol acetate was evaluated by measuring the disappearance of megestrol acetate by high-performance liquid chromatography with ultraviolet detection (HPLC-UV). The samples were analyzed on a Supelcosil LC-18 column (3μ, 120 Å, 3.0×100 mm). The flow rate was set to 0.3 mL/minute and the gradient method used is listed in Table 4 below.

TABLE 4

Gradient Method for HPLC

| Time (minute) | A % (10 mM Ammonium Formate) | B % (Acetonitrile) |
|---|---|---|
| 0.00 | 90.0 | 10.0 |
| 28.00 | 10.0 | 90.0 |
| 30.00 | 10.0 | 90.0 |
| 32.00 | 90.0 | 10.0 |
| 40.00 | 90.0 | 10.0 |

In evaluating the results, megestrol acetate was considered to be metabolized by a particular CYP isozyme if more than 20% of megestrol acetate disappeared from the incubation reaction mixture (i.e., <80% of megestrol acetate remained in the incubation reaction compared to metabolic negative controls).

Results for metabolism positive controls are reported in Tables 5-6. Specific activity for each CYP isoform was calculated based on the formation of metabolite from each CYP isoform-selective substrate.

Results for megestrol acetate metabolism by each CYP isozyme at either 5 or 50 μM using pooled human microsomes in the presence or absence of a CYP isozyme specific inhibitor are reported in Tables 7-9.

TABLE 5

Metabolic Positive Control in Pooled Human Liver Microsomes:
CYP1A2, CYP2A6, CYP2B6, CYP2C8 & CYP2C9

| CYP Isoform Specific Inhibitor Identification | Metabolite Formation | | | Specific Activity (pmol metabolite/min/pmol protein) | |
|---|---|---|---|---|---|
| | Raw (μM) | Adjusted (μM) | | | |
| | | Individual | Mean ± SD | Individual | Mean ± SD |
| Pooled Human Liver Microsomes - CYP1A2 | | | | | |
| Substrate: 50 μM Phenacetin, Metabolite: Acetaminophen, Incubation Time: 60 Minutes | | | | | |
| N/A | 2.89751 | 2.90 | 2.90 ± 0.0940 | 96.6 | 96.6 ± 3.13 |
| | 2.99336 | 2.99 | | 99.8 | |
| | 2.80546 | 2.81 | | 93.5 | |
| 5 μM Furafylline | 0.55448 | 0.554 | 0.593 ± 0.0333 | 18.5 | 19.8 ± 1.11 |
| | 0.61277 | 0.613 | | 20.4 | |
| | 0.61142 | 0.611 | | 20.4 | |
| Pooled Human Liver Microsomes - CYP2A6 | | | | | |
| Substrate: 8 μM Coumarin, Metabolite: 7-Hydroxycoumarin, Incubation Time: 60 Minutes | | | | | |
| N/A | 1.79002 | 1.79 | 2.16 ± 0.320 | 59.7 | 72.0 ± 10.7 |
| | 2.32317 | 2.32 | | 77.4 | |
| | 2.36315 | 2.36 | | 78.8 | |
| 10 μM Tranylcypromine | 0.58203 | 0.582 | 0.562 ± 0.0179 | 19.4 | 18.7 ± 0.597 |
| | 0.54770 | 0.548 | | 18.3 | |
| | 0.55607 | 0.556 | | 18.5 | |
| Pooled Human Liver Microsomes - CYP2B6 | | | | | |
| Substrate: 150 μM Bupropion, Metabolite: Hydroxybupropion, Incubation Time: 60 Minutes | | | | | |
| N/A | 6.32432 | 6.32 | 6.25 ± 0.0713 | 211 | 208 ± 2.38 |
| | 6.25001 | 6.25 | | 208 | |
| | 6.18183 | 6.18 | | 206 | |
| 1 μM Ticlopidine | 1.69214 | 1.69 | 1.71 ± 0.0220 | 56.4 | 56.9 ± 0.732 |
| | 1.69623 | 1.70 | | 56.5 | |
| | 1.73208 | 1.73 | | 57.7 | |
| Pooled Human Liver Microsomes - CYP2C8 | | | | | |
| Substrate: 5 μM Paclitaxel, Metabolite: 6-Hydroxypaclitaxel, Incubation Time: 60 Minutes | | | | | |
| N/A | 0.47876 | 0.479 | 0.443 ± 0.0345 | 19.9 | 18.5 ± 1.44 |
| | 0.44157 | 0.442 | | 18.4 | |
| | 0.40986 | 0.410 | | 17.1 | |
| 100 μM Quercetin | 0.06396 | 0.0640 | 0.0634 ± 0.00599 | 2.67 | 2.64 ± 0.250 |
| | 0.05718 | 0.0572 | | 2.38 | |
| | 0.06912 | 0.0691 | | 2.88 | |

TABLE 5-continued

Metabolic Positive Control in Pooled Human Liver Microsomes:
CYP1A2, CYP2A6, CYP2B6, CYP2C8 & CYP2C9

| CYP Isoform Specific Inhibitor Identification | Raw ($\mu$M) | Metabolite Formation Adjusted ($\mu$M) Individual | Mean ± SD | Specific Activity (pmol metabolite/min/pmol protein) Individual | Mean ± SD |
|---|---|---|---|---|---|
| \multicolumn{6}{c}{Pooled Human Liver Microsomes - CYP2C9} |
| \multicolumn{6}{c}{Substrate: 150 $\mu$M Tolbutamide, Metabolite: 4'-Methylhydroxytolbutamide, Incubation Time: 60 Minutes} |
| N/A | 2.72890 | 2.73 | 3.06 ± 0.304 | 91.0 | 102 ± 10.1 |
|  | 3.32551 | 3.33 |  | 111 |  |
|  | 3.12659 | 3.13 |  | 104 |  |
| 1.5 $\mu$M Sulfaphenazole | 1.05439 | 1.05 | 1.08 ± 0.0213 | 35.1 | 35.9 ± 0.711 |
|  | 1.08156 | 1.08 |  | 36.1 |  |
|  | 1.09648 | 1.10 |  | 36.5 |  |

Abbreviations: Conc., concentration; SD, standard deviation; Min, minute; N/A, not applicable Note:
For all calculations above, the resulting values are shown with at least three significant figures for display purposes only.

TABLE 6

Metabolic Positive Control in Pooled Human Liver Microsomes:
CYP2C19, CYP2D6, CYP2E1, & CYP3A4

| CYP Isoform Specific Inhibitor Identification | Raw ($\mu$M) | Metabolite Formation Adjusted ($\mu$M) Individual | Mean ± SD | Specific Activity (pmol metabolite/min/pmol protein) Individual | Mean ± SD |
|---|---|---|---|---|---|
| \multicolumn{6}{c}{Pooled Human Liver Microsomes - CYP2C19} |
| \multicolumn{6}{c}{Substrate: 50 $\mu$M S-Mephenytoin, Metabolite: 4'-Hydroxymephenytoin, Incubation Time: 60 Minutes} |
| N/A | 0.13018 | 0.130 | 0.133 ± 0.00289 | 4.34 | 4.45 ± 0.0962 |
|  | 0.13572 | 0.136 |  | 4.52 |  |
|  | 0.13435 | 0.134 |  | 4.48 |  |
| 80 $\mu$M Nootkatone | 0.02694[a] | <0.0500 | <0.0500 ± 0.000 | <1.67 | <1.67 ± 0.000 |
|  | 0.02825[a] | <0.0500 |  | <1.67 |  |
|  | 0.02324[a] | <0.0500 |  | <1.67 |  |
| \multicolumn{6}{c}{Pooled Human Liver Microsomes - CYP2D6} |
| \multicolumn{6}{c}{Substrate: 5 $\mu$M Dextromethorphan, Metabolite: Dextrorphan, Incubation Time: 60 Minutes} |
| N/A | 0.37638 | 0.376 | 0.388 ± 0.0125 | 12.5 | 12.9 ± 0.418 |
|  | 0.38683 | 0.387 |  | 12.9 |  |
|  | 0.40133 | 0.401 |  | 13.4 |  |
| 2 $\mu$M Quinidine | 0.07079 | 0.0708 | 0.0710 ± 0.000223 | 2.36 | 2.37 ± 0.00745 |
|  | 0.07090 | 0.0709 |  | 2.36 |  |
|  | 0.7122 | 0.0712 |  | 2.37 |  |
| \multicolumn{6}{c}{Pooled Human Liver Microsomes - CYP2E1} |
| \multicolumn{6}{c}{Substrate: 50 $\mu$M Chlorzoxazone, Metabolite: 6-Hydroxychlorzoxazone, Incubation Time: 60 Minutes} |
| N/A | 8.77640 | 8.78 | 8.35 ± 0.393 | 293 | 278 ± 13.1 |
|  | 8.00593 | 8.01 |  | 267 |  |
|  | 8.25741 | 8.26 |  | 275 |  |
| 100 $\mu$M DDC | 1.80463 | 1.80 | 1.77 ± 0.0341 | 60.2 | 58.9 ± 1.14 |
|  | 1.73846 | 1.74 |  | 57.9 |  |
|  | 1.75738 | 1.76 |  | 58.6 |  |
| \multicolumn{6}{c}{Pooled Human Liver Microsomes - CYP3A4} |
| \multicolumn{6}{c}{Substrate: 100 $\mu$M Testosterone, Metabolite: 6$\beta$-Hydroxytestosterone, Incubation Time: 60 Minutes} |
| N/A | 21.28945 | 21.3 | 20.0 ± 2.48 | 710 | 666 ± 82.7 |
|  | 21.51852 | 21.5 |  | 717 |  |
|  | 17.11313 | 17.1 |  | 570 |  |
| 1 $\mu$M Ketoconzole | 3.41131 | 3.41 | 3.45 ± 0.0397 | 114 | 115 ± 1.32 |
|  | 3.48924 | 3.49 |  | 116 |  |
|  | 3.46371 | 3.46 |  | 115 |  |

Abbreviations: Conc., concentration; SD, standard deviation; Min, minute; N/A, not applicable; DDC, Diethyldithiocarbamate

[a]The Raw value ($\mu$M) was below the lowest concentration on the standard curve (0.05 $\mu$M)

Note:
For all calculations above, the resulting values are shown with at least three significant figures for display purposes only.

TABLE 7

Metabolism of Megestrol Acetate in Pooled Human Liver Microsomes: CYP1A2, CYP2A6 & CYP2B6

| Megestrol Acetate (µM) | MNC Raw Data Observed (µM) | | Individual Raw Data Observed (µM) | Percent of Parent Disappearance | |
|---|---|---|---|---|---|
| | Individual | Mean ± SD | | Individual | Mean ± SD |
| Pooled Human Liver Microsomes: CYP1A2 | | | | | |
| 5 (with 1% acetonitrile) | 2.08794 2.42060 2.49166 | 2.33 ± 0.216 | 0.95474 0.82106 0.82007 | 59.1 64.8 64.9 | 62.9 ± 3.32 |
| 5 (with 5 µM Furafylline) | 2.46016 2.48146 2.61711 | 2.52 ± 0.0851 | 0.87164 0.84949 0.93966 | 65.4 66.3 62.7 | 64.8 ± 1.86 |
| 50 (with 1% acetonitrile) | 24.82979 25.01976 24.56842 | 24.8 ± 0.227 | 13.53736 12.96160 13.19828 | 45.4 47.7 46.8 | 46.7 ± 1.17 |
| 50 (with 5 µM Furafylline) | 24.52252 25.16412 25.06206 | 24.9 ± 0.345 | 12.86480 16.67944 18.07610 | 48.4 33.1 27.5 | 36.3 ± 10.8 |
| Pooled Human Liver Microsomes: CYP2A6 | | | | | |
| 5 (with 1% water) | 2.17483 2.17482 2.18283 | 2.18 ± 0.00462 | 0.42817 0.42708 0.45323 | 80.3 80.4 79.2 | 80.0 ± 0.679 |
| 5 (with 10 µM Tranylcypromine) | 2.30405 2.27518 2.22295 | 2.27 ± 0.0411 | 0.69952 0.68968 0.71652 | 69.1 69.6 68.4 | 69.0 ± 0.599 |
| 50 (with 1% water) | 18.32544 18.46336 18.34084 | 18.4 ± 0.0756 | 8.17062 8.24698 8.56217 | 55.5 55.1 53.4 | 54.7 ± 1.13 |
| 50 (with 10 µM Tranylcypromine) | 12.40454 11.65776 12.33542 | 12.1 ± 0.413 | 5.92681 6.26336 6.31432 | 51.1 48.4 48.0 | 49.2 ± 1.74 |
| Pooled Human Liver Microsomes: CYP2B6 | | | | | |
| 5 (with 1% methanol) | 2.44799 2.39621 2.39442 | 2.41 ± 0.0304 | 0.71311 0.70178 0.73579 | 70.4 70.9 69.5 | 70.3 ± 0.718 |
| 5 (with 1 µM Ticlopidine) | 2.41974 2.35679 2.31618 | 2.36 ± 0.0522 | 0.64641 0.66339 0.67593 | 72.7 71.9 71.4 | 72.0 ± 0.627 |
| 50 (with 1% methanol) | 18.42479 19.56180 18.50095 | 18.8 ± 0.636 | 8.51293 8.88317 9.15195 | 54.8 52.8 51.4 | 53.0 ± 1.70 |
| 50 (with 1 µM Ticlopidine) | 16.26409 17.11550 16.89851 | 16.8 ± 0.442 | 7.09651 8.04262 8.40584 | 57.7 52.0 49.8 | 53.2 ± 4.03 |

Abbreviations: SD, standard deviation; MNC, metabolic negative control
Note:
For all calculations above, the resulting values are shown with at least three significant figures for display purposes only.

TABLE 8

Metabolism of Megestrol Acetate in Pooled Human Liver Microsomes: CYP2C8, CYP2C9 & CYP2C19

| Megestrol Acetate (µM) | MNC Raw Data Observed (µM) | | Individual Raw Data Observed (µM) | Percent of Parent Disappearance | |
|---|---|---|---|---|---|
| | Individual | Mean ± SD | | Individual | Mean ± SD |
| Pooled Human Liver Microsomes: CYP2C8 | | | | | |
| 5 (with 0.1% DMSO) | 2.35289 2.30765 2.33029 | 2.33 ± 0.0226 | 1.09460 1.07572 1.11022 | 53.0 53.8 52.4 | 53.1 ± 0.741 |
| 5 (with 100 µM Quercetin) | 2.16316 2.12785 2.11143 | 2.13 ± 0.0264 | 1.97040 1.97463 2.01549 | 7.67 7.47 5.56 | 6.90 ± 1.17 |
| 50 (with 0.1% DMSO) | 22.26014 23.10418 23.21799 | 22.9 ± 0.523 | 13.41870 13.86224 13.47016 | 41.3 39.4 41.1 | 40.6 ± 1.06 |
| 50 (with 100 µM Quercetin) | 21.96589 22.34904 22.28027 | 22.2 ± 0.204 | 20.53214 21.39614 22.17737 | 7.51 3.61 0.0947 | 3.74 ± 3.71 |

TABLE 8-continued

Metabolism of Megestrol Acetate in Pooled Human Liver Microsomes: CYP2C8, CYP2C9 & CYP2C19

| Megestrol Acetate | MNC Raw Data Observed (μM) | | Individual Raw Data | Percent of Parent Disappearance | |
|---|---|---|---|---|---|
| (μM) | Individual | Mean ± SD | Observed (μM) | Individual | Mean ± SD |
| Pooled Human Liver Microsomes: CYP2C9 | | | | | |
| 5 (with 1% water) | 2.08085 2.38759 2.42156 | 2.30 ± 0.188 | 0.71931 0.74531 0.75224 | 68.7 67.5 67.2 | 67.8 ± 0.756 |
| 5 (with 1.5 μM Sulfaphenazole) | 2.62566 2.36577 2.45537 | 2.48 ± 0.132 | 0.76954 0.76926 0.80028 | 69.0 69.0 67.8 | 68.6 ± 0.718 |
| 50 (with 1% water) | 18.48713 19.18851 20.26637 | 19.3 ± 0.896 | 10.56006 8.65022 8.93315 | 45.3 55.2 53.7 | 51.4 ± 5.34 |
| 50 (with 1.5 μM Sulfaphenazole) | 18.33626 19.27974 26.37132 | 21.3 ± 4.39 | 9.27156 9.37276 9.65444 | 56.5 56.1 54.7 | 55.8 ± 0.930 |
| Pooled Human Liver Microsomes: CYP2C19 | | | | | |
| 5 (with 1% methanol) | 2.39596 2.37671 2.40281 | 2.39 ± 0.0135 | 0.69796 0.71812 0.72792 | 70.8 70.0 69.6 | 70.1 ± 0.639 |
| 5 (with 80 μM Nootkatone) | 2.45508 2.50601 2.50490 | 2.49 ± 0.0291 | 0.66695 0.79226 0.68246 | 73.2 68.2 72.6 | 71.3 ± 2.74 |
| 50 (with 1% methanol) | 21.91871 22.30950 22.11633 | 22.1 ± 0.195 | 10.91805 10.93385 11.27449 | 50.6 50.6 49.0 | 50.1 ± 0.911 |
| 50 (with 80 μM Nootkatone) | 21.03328 27.07804 22.04331 | 23.4 ± 3.24 | 11.36478 11.98487 12.71524 | 51.4 48.7 45.6 | 48.6 ± 2.89 |

Abbreviations: SD, standard deviation; MNC, metabolic negative control
Note:
For all calculations above, the resulting values are shown with at least three significant figures for display purposes only.

TABLE 9

Metabolism of Megestrol Acetate in Pooled Human Liver Microsomes: CYP2D6, CYP2E1 & CYP3A4

| Megestrol Acetate | MNC Raw Data Observed (μM) | | Individual Raw Data | Percent of Parent Disappearance | |
|---|---|---|---|---|---|
| (μM) | Individual | Mean ± SD | Observed (μM) | Individual | Mean ± SD |
| Pooled Human Liver Microsomes: CYP2D6 | | | | | |
| 5 (with 1% methanol) | 1.97816 2.31368 2.36645 | 2.22 ± 0.211 | 0.72973 0.73795 0.75004 | 67.1 66.8 66.2 | 66.7 ± 0.460 |
| 5 (with 2 μM Quinidine) | 2.48941 2.48896 2.48249 | 2.49 ± 0.00387 | 0.81441 0.81642 0.82170 | 67.3 67.2 67.0 | 67.1 ± 0.151 |
| 50 (with 1% methanol) | 22.95356 22.19211 22.39222 | 22.5 ± 0.395 | 10.60919 11.27300 11.76624 | 52.9 49.9 47.7 | 50.2 ± 2.58 |
| 50 (with 2 μM Quinidine) | 21.88764 24.69687 22.39984 | 23.0 ± 1.50 | 10.72360 11.33815 11.26793 | 53.4 50.7 51.0 | 51.7 ± 1.46 |
| Pooled Human Liver Microsomes: CYP2E1 | | | | | |
| 5 (with 1% water) | 2.45271 2.34190 2.39212 | 2.40 ± 0.0555 | 0.42548 0.45786 0.45287 | 82.2 80.9 81.1 | 81.4 ± 0.728 |
| 5 (with 100 μM DDC) | 2.34522 2.34667 2.37959 | 2.36 ± 0.0194 | 1.10733 1.07692 1.07722 | 53.0 54.3 54.3 | 53.9 ± 0.741 |
| 50 (with 1% water) | 21.33816 21.75360 21.87651 | 21.7 ± 0.282 | 8.91726 9.21199 9.38393 | 58.8 57.5 56.7 | 57.7 ± 1.09 |
| 50 (with 100 μM DDC) | 17.53610 18.17593 18.03079 | 17.9 ± 0.335 | 15.40250 16.16200 16.10589 | 14.0 9.78 10.1 | 11.3 ± 2.36 |

TABLE 9-continued

Metabolism of Megestrol Acetate in Pooled Human Liver Microsomes: CYP2D6, CYP2E1 & CYP3A4

| Megestrol Acetate ($\mu$M) | MNC Raw Data Observed ($\mu$M) | | Individual Raw Data Observed ($\mu$M) | Percent of Parent Disappearance | |
|---|---|---|---|---|---|
| | Individual | Mean ± SD | | Individual | Mean ± SD |
| Pooled Human Liver Microsomes: CYP3A4 | | | | | |
| 5 | 2.48245 | 2.44 ± 0.0397 | 0.71651 | 70.6 | 68.7 ± 1.86 |
| (with 1% | 2.40977 | | 0.76445 | 68.6 | |
| acetonitrile) | 2.41851 | | 0.80718 | 66.9 | |
| 5 | 2.39299 | 2.44 ± 0.0422 | 2.15110 | 11.9 | 10.9 ± 3.30 |
| (with 1 $\mu$M | 2.46772 | | 2.11193 | 13.5 | |
| Ketoconazole) | 2.46434 | | 2.26669 | 7.17 | |
| 50 | 19.92398 | 20.5 ± 0.517 | 9.54893 | 53.4 | 49.6 ± 3.36 |
| (with 1% | 20.72202 | | 10.61008 | 48.3 | |
| acetonitrile) | 20.89240 | | 10.84385 | 47.1 | |
| 50 | 15.93628 | 15.6 ± 0.476 | 14.33617 | 7.86 | 6.82 ± 4.47 |
| (with 1 $\mu$M | 15.02473 | | 13.89992 | 10.7 | |
| Ketoconazole) | 15.71845 | | 15.26160 | 1.92 | |

Abbreviations: SD, standard deviation; MNC, metabolic negative control; DDC, Diethyldithiocarbamate
Note:
For all calculations above, the resulting values are shown with at least three significant figures for display purposes only.

The chemical inhibitors and the concentrations chosen were suitable for evaluating the contributions of specific CYP isoforms towards the metabolism of megestrol acetate. As can be seen in Tables 5 and 6, the known chemical inhibitors of CYP enzyme activities significantly inhibited specific CYP isoform activities in pooled human liver microsomes (Tables 5 and 6, compare specific activity of each CYP isoform in the presence and absence of CYP isoform specific inhibitor). Specifically, CYP1A2 activity was decreased from 96.6±3.13 pmol metabolite/minute/mg protein to 19.8±1.11 pmol metabolite/minute/mg protein by 5 $\mu$M furafylline. CYP2A6 activity was decreased from 72.0±10.7 pmol metabolite/minute/mg protein to 18.7±0.597 pmol metabolite/minute/mg protein by 10 $\mu$M tranylcypromine. CYP2B6 activity was decreased from 208±2.38 pmol metabolite/minute/mg protein to 56.9±0.732 pmol metabolite/minute/mg protein by 1 $\mu$M ticlopidine. CYP2C8 activity was decreased from 18.5±1.44 pmol metabolite/minute/mg protein to 2.64±0.250 pmol metabolite/minute/mg protein by 100 $\mu$M quercetin. CYP2C9 activity was decreased from 102±10.1 pmol metabolite/minute/mg protein to 35.9±0.711 pmol metabolite/minute/mg protein by 1.5 $\mu$M sulfaphenazole. CYP2C19 activity was decreased from 4.45±0.0962 pmol metabolite/minute/mg protein to <1.67±0.000 pmol metabolite/minute/mg protein by 80 $\mu$M nootkatone. CYP2D6 activity was decreased from 12.9±0.418 pmol metabolite/minute/mg protein to 2.37±0.00745 pmol metabolite/minute/mg protein by 2 $\mu$M quinidine. CYP2E1 activity was decreased from 278±13.1 pmol metabolite/minute/mg protein to 58.9±1.14 pmol metabolite/minute/mg protein by 100 $\mu$M diethyldithiocarbamate. CYP3A4 activity was decreased from 666±82.7 pmol metabolite/minute/mg protein to 115±1.32 pmol metabolite/minute/mg protein by 1 $\mu$M ketoconazole.

CYP1A2 does not seem to contribute to megestrol acetate metabolism based on the metabolism data obtained from pooled human microsomes in the presence and absence of furafylline, a CYP1A2 specific inhibitor. Megestrol acetate was significantly (>20%) metabolized in pooled human liver microsomes (Table 7). In the presence of 5 $\mu$M furafylline, the percent of megestrol acetate metabolized does not differ from the percentage of megestrol acetate metabolized in the absence of the inhibitor at a statistically significant level (p>0.05 using an unpaired two-tailed t-test). Similarly, in the presence of 50 $\mu$M furafylline, the percent of megestrol acetate metabolized is not different from the percentage of megestrol acetate metabolized in the absence of the inhibitor at a statistically significant level (p>0.05 using an unpaired two-tailed t-test).

CYP2A6 may contribute to megestrol acetate metabolism under the experimental conditions. Megestrol acetate was significantly (>20%) metabolized in pooled human liver microsomes (Table 7). In the presence of both concentrations of tranylcypromine, the percentage of megestrol acetate metabolized was less than that of the percentage of megestrol acetate metabolized in the absence of the inhibitor at a statistically significant level (p<0.05 using an unpaired two-tailed t-test), indicating that the metabolism of megestrol acetate was inhibited by the inhibitor tranylcypromine in the pooled human liver microsomes.

CYP2B6 does not contribute to megestrol acetate metabolism under the experimental conditions. In the presence of 1 $\mu$M ticlopidine, the percent of megestrol acetate metabolized was 72.0±0.627 and 53.2±4.03, at 5 $\mu$M and 50 $\mu$M, respectively (Table 7) as opposed to 70.3±0.718% and 53.0±1.70% in the vehicle control groups, at 5 $\mu$M and 50 $\mu$M, respectively.

CYP2C8 appears to contribute to megestrol acetate metabolism under these experimental conditions. Megestrol acetate was significantly (>20%) metabolized in pooled human liver microsomes (Table 8). In the presence of both concentrations of quercetin, the percentage of megestrol acetate metabolized was less than that of the percentage of megestrol acetate metabolized in the absence of the inhibitor at a statistically significant level (p<0.05 using an unpaired two-tailed t-test).

CYP2C9 does not seem to contribute to megestrol acetate metabolism based on the metabolism data obtained from pooled human microsomes in the presence and absence of sulfaphenazole, a CYP2C9 specific inhibitor. Megestrol acetate was significantly (>20%) metabolized in pooled human liver microsomes (Table 8). In the presence of both concentrations of sulfaphenazole, the percentage of megestrol acetate metabolized was not different from the percentage of megestrol acetate metabolized in the absence of the inhibitor at a statistically significant level (p>0.05 using an unpaired two-tailed t-test).

CYP2C19 appears not to be contributing to megestrol acetate metabolism based on the metabolism data obtained from pooled human microsomes in the presence and absence of nootkatone, a CYP2C19 specific inhibitor. Megestrol acetate was significantly (>20%) metabolized in pooled human liver microsomes (Table 8). In the presence of both concentrations of nootkatone, the percentage of megestrol acetate metabolized was not different from the percentage of megestrol acetate metabolized in the absence of the inhibitor at a statistically significant level ($p>0.05$ using an unpaired two-tailed t-test).

CYP2D6 does not seem to contribute to megestrol acetate metabolism based on the metabolism data obtained from pooled human microsomes in the presence and absence of quinidine, a CYP2D6 specific inhibitor. Megestrol acetate was significantly (>20%) metabolized in pooled human liver microsomes (Table 9). In the presence of both concentrations of quinidine, the percentage of megestrol acetate metabolized was not different from the percentage of megestrol acetate metabolized in the absence of the inhibitor at a statistically significant level ($p>0.05$ using an unpaired two-tailed t-test).

CYP2E1 appears to contribute to megestrol acetate metabolism under the experimental conditions. Megestrol acetate was significantly (>20%) metabolized in pooled human liver microsomes (Table 9). In the presence of both concentrations of diethyldithiocarbamate, a CYP2E1 specific inhibitor, the percentage of megestrol acetate metabolized was less than that of the percentage of megestrol acetate metabolized in the absence of the inhibitor at a statistically significant level ($p<0.05$ using an unpaired two-tailed t-test).

CYP3A4 seems to contribute to megestrol acetate metabolism under the experimental conditions. Megestrol acetate was significantly (>20%) metabolized in pooled human liver microsomes (Table 9). In the presence of both concentrations of ketoconazole, a CYP3A4 specific inhibitor, the percentage of megestrol acetate metabolized was less than that of the percentage of megestrol acetate metabolized in the absence of the inhibitor at a statistically significant level ($p<0.05$ using an unpaired two-tailed t-test), indicating that the metabolism of megestrol acetate was inhibited by the CYP3A4 specific inhibitor in the pooled human liver microsomes.

Example 2

Metabolism of Megestrol Acetate by Individual Recombinant Human Cytochrome p450 Isozymes (SUPERSOMES™)

These experiments were conducted to determine which specific Cytochrome p450 isozymes are capable of metabolizing megestrol acetate. In this study, individual CYP isoforms expressed from human cDNA and P450 reductase cDNA were used (BD SUPERSOMES™ Enzymes, BD Biosciences Discovery Labware, Woburn, Mass.). SUPERSOMES™ are microsomes from baculovirus-infected insect cells containing singly expressed recombinant human CYP enzymes.

In this study, incubation mixtures containing SUPERSOMES™ containing individually expressed CYP1A2, CYP2A6, CYP2B6, CYP2C8, CYP2C9, CYP2C19, CYP2D6, CYP2E1, or CYP3A4 enzymes at 5 or 20 pmol cytochrome p450 were incubated in a Tris or phosphate buffer as recommended by the manufacturer and megestrol acetate at concentrations 5 or 50 µM. After a 5 minute preincubation, NRS was added to the incubation mixtures to initiate reactions. The final incubation volume was 0.5 mL. Incubations were continued for 60 minutes. NRS components for these experiments were 3.3 mM glucose-6-phosphate, 0.4 U/mL glucose-6-phosphate dehydrogenase, 3.3 mM magnesium chloride and the appropriate NADP+ concentration and incubation buffer as listed in the table below:

| CYP Identification | NADP+ | Incubation Buffer |
|---|---|---|
| 1A2, 2D6, 3A4 | 1.3 mM | 100 mM Potassium Phosphate |
| 2B6, 2C8, 2C19, 2E1 | 1.3 mM | 50 mM Potassium Phosphate |
| 2C9 | 1.3 mM | 100 mM Tris |
| 2A6 | 0.065 mM | 50 mM Tris |

Matrix controls were prepared in the appropriate buffer containing SUPERSOMES™ containing individually expressed CYP1A2, CYP2A6, CYP2B6, CYP2C8, CYP2C9, CYP2C19, CYP2D6, CYP2E1, or CYP3A4 enzymes at 5 or 20 pmol cytochrome p450 and 1% acetonitrile. After a 5 minute preincubation, NRS was added to the incubation mixtures to initiate the reactions. The final incubation volume was 0.5 mL. Incubations were continued for 60 minutes.

Metabolic positive controls were prepared in the appropriate buffer containing SUPERSOMES™ containing individually expressed CYP1A2, CYP2A6, CYP2B6, CYP2C8, CYP2C9, CYP2C19, CYP2D6, CYP2E1, or CYP3A4 enzymes at 5 or 20 pmol cytochrome p450 and a CYP isoform-selective substrate. After a 5 minute preincubation, NRS was added to the incubation mixtures to initiate reactions. The final volume and incubation time are as described above. The final substrate concentrations, solvents, metabolite formed from each isoform-selective substrate, and metabolite assay methods are as listed in Table 3.

Metabolic negative controls were prepared in the appropriate buffer containing SUPERSOMES™ containing individually expressed CYP1A2, CYP2A6, CYP2B6, CYP2C8, CYP2C9, CYP2C19, CYP2D6, CYP2E1, or CYP3A4 enzymes at 5 or 20 pmol cytochrome p450 and megestrol acetate at concentrations 5 or 50 µM. After a 5-minute preincubation, an appropriate amount of the appropriate buffer was added to the reaction mixtures to make the final volume of 0.5 mL. The incubations were continued for 60 minutes.

All incubations were conducted at 37±1° C. in a shaking water bath and were carried out in triplicates.

All incubation reactions were terminated by adding 0.5 mL methanol, and the samples were transferred to cryovials and stored at −70±10° C. until analysis.

The metabolism of megestrol acetate by individual CYP isozyme was evaluated by measuring the disappearance of megestrol acetate using high-performance liquid chromatography with ultraviolet detection (HPLC/UV). In incubation reactions containing 50 µM and 20 pmol CYP isoenzyme, the metabolism of megestrol acetate by individual CYP isozyme was further evaluated by measuring the formation of megestrol acetate metabolite(s) using liquid chromatography/mass spectrometry (LC/MS). Liquid chromatography parameters are as listed in Table 4.

In evaluating megestrol acetate metabolism by individual CYP isoenzymes, megestrol acetate was considered to be metabolized by a particular CYP isoenzyme if more than 20% of megestrol acetate was depleted from the incubation reaction mixture (i.e., <80% of megestrol acetate remained in the incubation reaction compared to metabolic negative controls). Additionally, when metabolism was evaluated by the formation of megestrol acetate metabolite(s), megestrol acetate is considered to be metabolized by a particular CYP isoenzyme if more than 1% of the megestrol acetate was converted to its metabolite(s) by that CYP isozyme.

In this Example, megestrol acetate and CYP selective substrates were prepared as described in Example 1.

Metabolic positive controls in individual recombinant human CYP isozyme are reported in Tables 10-11.

The results for megestrol acetate metabolism by individual recombinant human CYP isoenzyme as measured by megestrol acetate disappearance at either 5 or 50 μM in incubations containing either 5 or 20 pmol of a recombinant cytochrome p450 isozyme are reported in Tables 12-16.

TABLE 10

Metabolic Positive Control in Recombinant Human Cytochrome P450 Enzymes (SUPERSOMES ™): CYP1A2, CYP2A6, CYP2B6, CYP2C8 & CYP2C9

| Recombinant Human Cytochrome P450 Enzyme Content (pmol) | Metabolite Formation | | | Specific Activity (pmol metabolite/min/pmol protein) | |
|---|---|---|---|---|---|
| | Raw (μM) | Adjusted (μM) Individual | Mean ± SD | Individual | Mean ± SD |
| Human CYP1A2 + P450 Reductase SUPERSOMES ™ Substrate: 50 μM Phenacetin, Metabolite: Acetaminophen, Incubation Time: 60 Minutes | | | | | |
| 5 | 3.82114 | 3.82 | 3.72 ± 0.132 | 12.7 | 12.4 ± 0.441 |
| | 3.77207 | 3.77 | | 12.6 | |
| | 3.57168 | 3.57 | | 11.9 | |
| 20 | 10.39907 | 10.4 | 10.2 ± 0.154 | 8.67 | 8.53 ± 0.129 |
| | 10.22736 | 10.2 | | 8.52 | |
| | 10.09110 | 10.1 | | 8.41 | |
| Human CYP2A6 + P450 Reductase + Cytochrome $b_5$ SUPERSOMES ™ Substrate: 8 μM Coumarin, Metabolite: 7-Hydroxycoumarin, Incubation Time: 60 Minutes | | | | | |
| 5 | 0.58277 | 0.583 | 0.568 ± 0.0130 | 1.94 | 1.89 ± 0.0434 |
| | 0.55846 | 0.558 | | 1.86 | |
| | 0.56247 | 0.562 | | 1.87 | |
| 20 | 2.19308 | 2.19 | 2.21 ± 0.0187 | 1.83 | 1.84 ± 0.0156 |
| | 2.23021 | 2.23 | | 1.86 | |
| | 2.21608 | 2.22 | | 1.85 | |
| Human CYP2B6 + P450 Reductase + Cytochrome $b_5$ SUPERSOMES ™ Substrate: 150 μM Bupropion, Metabolite: Hydroxybupropion, Incubation Time: 60 Minutes | | | | | |
| 5 | 2.11849 | 2.12 | 2.22 ± 0.120 | 7.06 | 7.40 ± 0.400 |
| | 2.19237 | 2.19 | | 7.31 | |
| | 2.35309 | 2.35 | | 7.84 | |
| 20 | 8.34132 | 8.34 | 9.10 ± 0.676 | 6.95 | 7.58 ± 0.564 |
| | 9.30040 | 9.30 | | 7.75 | |
| | 9.64668 | 9.65 | | 8.04 | |
| Human CYP2C8 + P450 Reductase + Cytochrome $b_5$ SUPERSOMES ™ Substrate: 5 μM Paclitaxel, Metabolite: 6-Hydroxypaclitaxel, Incubation Time: 60 Minutes | | | | | |
| 5 | 0.43556 | 0.436 | 0.403 ± 0.0317 | 1.81 | 1.68 ± 0.132 |
| | 0.40146 | 0.401 | | 1.67 | |
| | 0.37223 | 0.372 | | 1.55 | |
| 20 | 1.22300 | 1.22 | 1.13 ± 0.115 | 1.27 | 1.17 ± 0.119 |
| | 1.00065 | 1.00 | | 1.04 | |
| | 1.15979 | 1.16 | | 1.21 | |
| Human CYP2C9*1 ($Arg_{144}$) + P450 Reductase + Cytochrome $b_5$ SUPERSOMES ™ Substrate: 150 μM Tolbutamide, Metabolite: 4'-Methylhydroxytolbutamide, Incubation Time: 60 Minutes | | | | | |
| 5 | 0.33108 | 0.331 | 0.298 ± 0.0352 | 1.10 | 0.992 ± 0.117 |
| | 0.30078 | 0.301 | | 1.00 | |
| | 0.26098 | 0.261 | | 0.870 | |
| 20 | 1.36872 | 1.37 | 1.37 ± 0.0264 | 1.14 | 1.14 ± 0.0220 |
| | 1.33873 | 1.34 | | 1.12 | |
| | 1.39133 | 1.39 | | 1.16 | |

Abbreviations: Conc., concentration; SD, standard deviation; Min, minute

Note:
For all calculations above, the resulting values are shown with at least three significant figures for display purposes only.

TABLE 11

Metabolic Positive Control in Recombinant Human Cytochrome P450 Enzymes (SUPERSOMES ™): CYP2C19, CYP2D6, CYP2E1, & CYP3A4

| Recombinant Human Cytochrome P450 Enzyme Content (pmol) | Metabolite Formation | | | Specific Activity (pmol metabolite/min/pmol protein) | |
|---|---|---|---|---|---|
| | Raw (µM) | Adjusted (µM) Individual | Mean ± SD | Individual | Mean ± SD |
| *Human CYP2C19 + P450 Reductase + Cytochrome $b_5$ SUPERSOMES ™* | | | | | |
| *Substrate: 50 µM S-Mephenytoin, Metabolite: 4'-Hydroxymephenytoin, Incubation Time: 60 Minutes* | | | | | |
| 5 | 0.74098 | 0.741 | 0.730 ± 0.0114 | 2.47 | 2.43 ± 0.0380 |
|   | 0.71819 | 0.718 |  | 2.39 |  |
|   | 0.72962 | 0.730 |  | 2.43 |  |
| 20 | 1.89062 | 1.89 | 1.95 ± 0.0647 | 1.58 | 1.63 ± 0.0539 |
|   | 2.01931 | 2.02 |  | 1.68 |  |
|   | 1.94269 | 1.94 |  | 1.62 |  |
| *Human CYP2D6*1 + P450 Reductase SUPERSOMES ™* | | | | | |
| *Substrate: 5 µM Dextromethorphan, Metabolite: Dextrorphan, Incubation Time: 60 Minutes* | | | | | |
| 5 | 1.68735 | 1.69 | 1.64 ± 0.0909 | 5.62 | 5.46 ± 0.303 |
|   | 1.53181 | 1.53 |  | 5.11 |  |
|   | 1.69116 | 1.69 |  | 5.64 |  |
| 20 | 1.09336 | 1.09 | 1.00 ± 0.161 | 0.911 | 0.837 ± 0.135 |
|   | 1.10293 | 1.10 |  | 0.919 |  |
|   | 0.81861 | 0.819 |  | 0.682 |  |
| *Human CYP2E1 + P450 Reductase + Cytochrome $b_5$ SUPERSOMES ™* | | | | | |
| *Substrate: 50 µM Chlorzoxazone, Metabolite: 6-Hydroxychlorzoxazone, Incubation Time: 60 Minutes* | | | | | |
| 5 | 3.55787 | 3.56 | 3.49 ± 0.0817 | 11.9 | 11.96 ± 0.272 |
|   | 3.39821 | 3.40 |  | 11.3 |  |
|   | 3.50790 | 3.51 |  | 11.7 |  |
| 20 | 5.34743 | 5.35 | 4.99 ± N/A | 4.46 | 4.16 ± N/A |
|   | 4.64073 | 4.64 |  | 3.87 |  |
|   | N/A* | N/A* |  | N/A |  |
| *Human CYP3A4 + P450 Reductase + Cytochrome $b_5$ SUPERSOMES ™* | | | | | |
| *Substrate: 100 µM Testosterone, Metabolite: 6β-Hydroxytestosterone, Incubation Time: 60 Minutes* | | | | | |
| 5 | 8.98884 | 8.99 | 10.1 ± 0.936 | 30.0 | 33.5 ± 3.12 |
|   | 10.47609 | 10.5 |  | 34.9 |  |
|   | 10.71696 | 10.7 |  | 35.7 |  |
| 20 | 30.32236 | 30.3 | 30.6 ± 0.238 | 25.3 | 25.5 ± 0.199 |
|   | 30.75906 | 30.8 |  | 25.6 |  |
|   | 30.70583 | 30.7 |  | 25.6 |  |

Abbreviations: Conc., concentration; SD, standard deviation; Min, minute
*Sample not available for analysis due to incubation error.
Note:
For all calculations above, the resulting values are shown with at least three significant figures for display purposes only.

TABLE 12

Metabolism of Megestrol Acetate in Recombinant Human Cytochrome P450 Enzymes (SUPERSOMES ™): CYP1A2 & CYP2A6

| Megestrol Acetate (µM) | MNC Raw Data Observed (µM) | | Individual Raw Data Observed (µM) | Percent of Parent Disappearance | |
|---|---|---|---|---|---|
| | Individual | Mean ± SD | | Individual | Mean ± SD |
| *Human CYP1A2 + P450 Reductase SUPERSOMES ™ -* | | | | | |
| *5 pmol Recombinant Human Cytochrome P450 Enzyme Content* | | | | | |
| 5 | 1.95731 | 1.99 ± 0.0385 | 2.04356 | −2.76 | −7.99 ± 4.60 |
|   | 1.97689 |  | 2.18331 | −9.79 |  |
|   | 2.03154 |  | 2.21578 | −11.4 |  |
| 50 | 19.32206 | 19.1 ± 0.310 | 20.03416 | −5.05 | −4.04 ± 1.72 |
|   | 18.72425 |  | 20.02704 | −5.02 |  |
|   | 19.16482 |  | 19.46128 | −2.05 |  |
| *Human CYP1A2 + P450 Reductase SUPERSOMES ™ -* | | | | | |
| *20 pmol Recombinant Human Cytochrome P450 Enzyme Content* | | | | | |
| 5 | 2.56252 | 2.44 ± 0.104 | 2.30905 | 5.51 | 6.45 ± 1.18 |
|   | 2.39994 |  | 2.29536 | 6.07 |  |
|   | 2.36856 |  | 2.25360 | 7.78 |  |

TABLE 12-continued

Metabolism of Megestrol Acetate in Recombinant Human Cytochrome P450 Enzymes (SUPERSOMES ™): CYP1A2 & CYP2A6

| Megestrol Acetate (μM) | MNC Raw Data Observed (μM) | | Individual Raw Data Observed (μM) | Percent of Parent Disappearance | |
|---|---|---|---|---|---|
| | Individual | Mean ± SD | | Individual | Mean ± SD |
| 50 | 21.19143 | 22.0 ± 1.63 | 19.60069 | 11.0 | 7.51 ± 3.06 |
| | 23.89692 | | 20.85760 | 5.29 | |
| | 20.98099 | | 20.64799 | 6.24 | |
| Human CYP2A6 + P450 Reductase + Cytochrome b5 SUPERSOMES ™ - 5 pmol Recombinant Human Cytochrome P450 Enzyme Content | | | | | |
| 5 | 2.43962 | 2.41 ± 0.0271 | 2.31285 | 3.96 | 0.486 ± 4.76 |
| | 2.39194 | | 2.34968 | 2.43 | |
| | 2.39338 | | 2.52728 | −4.94 | |
| 50 | 23.41203 | 23.6 ± 0.724 | 24.75040 | −5.02 | −1.14 ± 3.38 |
| | 24.35498 | | 23.30408 | 1.11 | |
| | 22.93198 | | 23.45221 | 0.484 | |
| Human CYP2A6 + P450 Reductase + Cytochrome b5 SUPERSOMES ™ - 20 pmol Recombinant Human Cytochrome P450 Enzyme Content | | | | | |
| 5 | 2.55905 | 2.49 ± 0.0651 | 2.45594 | 1.36 | −2.11 ± 4.98 |
| | 2.42980 | | 2.48652 | 0.129 | |
| | 2.48034 | | 2.68430 | −7.81 | |
| 50 | 22.22265 | 22.8 ± 0.694 | 21.73788 | 4.54 | 1.10 ± 3.16 |
| | 22.54305 | | 22.67670 | 0.420 | |
| | 23.55158 | | 23.15004 | −1.66 | |

Abbreviations: SD, standard deviation; MNC, metabolic negative control
Note:
For all calculations above, the resulting values are shown with at least three significant figures for display purposes only.

TABLE 13

Metabolism of Megestrol Acetate in Recombinant Human Cytochrome P450 Enzymes (SUPERSOMES ™): CYP2B6 & CYP2C8

| Megestrol Acetate (μM) | MNC Raw Data Observed (μM) | | Individual Raw Data Observed (μM) | Percent of Parent Disappearance | |
|---|---|---|---|---|---|
| | Individual | Mean ± SD | | Individual | Mean ± SD |
| Human CYP2B6 + P450 Reductase + Cytochrome b$_5$ SUPERSOMES ™ - 5 pmol Recombinant Human Cytochrome P450 Enzyme Content | | | | | |
| 5 | 2.17602 | 2.21 ± 0.0336 | 2.22133 | −0.459 | −2.98 ± 2.20 |
| | 2.21462 | | 2.29969 | −4.00 | |
| | 2.24291 | | 2.31043 | −4.49 | |
| 50 | 21.24634 | 21.7 ± 1.14 | 20.88121 | 3.63 | −5.73 ± 12.5 |
| | 20.79678 | | 21.85378 | −0.862 | |
| | 22.95821 | | 25.99109 | −20.0 | |
| Human CYP2B6 + P450 Reductase + Cytochrome b$_5$ SUPERSOMES ™ - 20 pmol Recombinant Human Cytochrome P450 Enzyme Content | | | | | |
| 5 | 2.53272 | 2.47 ± 0.0566 | 2.47440 | −0.257 | 2.21 ± 2.14 |
| | 2.42761 | | 2.38129 | 3.52 | |
| | 2.44387 | | 2.38499 | 3.37 | |
| 50 | 21.66064 | 22.7 ± 0.929 | 21.46343 | 5.33 | 2.53 ± 2.43 |
| | 23.48878 | | 22.47392 | 0.869 | |
| | 22.86352 | | 22.35321 | 1.40 | |
| Human CYP2C8 + P450 Reductase + Cytochrome b$_5$ SUPERSOMES ™ - 5 pmol Recombinant Human Cytochrome P450 Enzyme Content | | | | | |
| 5 | 2.28497 | 2.21 ± 0.0622 | 2.20172 | 0.539 | −18.0 ± 18.6 |
| | 2.18503 | | 3.02489 | −36.6 | |
| | 2.17095 | | 2.60932 | −17.9 | |
| 50 | 21.32839 | 21.6 ± 0.249 | 21.39732 | 1.01 | −3.32 ± 3.78 |
| | 21.75727 | | 22.90115 | −5.95 | |
| | 21.76226 | | 22.69917 | −5.01 | |
| Human CYP2C8 + P450 Reductase + Cytochrome b$_5$ SUPERSOMES ™ - 20 pmol Recombinant Human Cytochrome P450 Enzyme Content | | | | | |
| 5 | 2.02913 | 1.98 ± 0.0451 | 1.94023 | 2.05 | −0.468 ± 2.66 |
| | 1.97385 | | 1.98488 | −0.201 | |
| | 1.93971 | | 2.04540 | −3.26 | |

TABLE 13-continued

Metabolism of Megestrol Acetate in Recombinant Human Cytochrome P450 Enzymes (SUPERSOMES ™): CYP2B6 & CYP2C8

| Megestrol Acetate | MNC Raw Data Observed (μM) | | Individual Raw Data Observed | Percent of Parent Disappearance | |
|---|---|---|---|---|---|
| (μM) | Individual | Mean ± SD | (μM) | Individual | Mean ± SD |
| 50 | 18.74901 | 19.6 ± 0.733 | 19.69437 | −0.513 | −3.62 ± 2.70 |
|  | 20.06834 |  | 20.63881 | −5.33 |  |
|  | 19.96412 |  | 20.57720 | −5.02 |  |

Abbreviations: SD, standard deviation; MNC, metabolic negative control

Note:

For all calculations above, the resulting values are shown with at least three significant figures for display purposes only.

TABLE 14

Metabolism of Megestrol Acetate in Recombinant Human Cytochrome P450 Enzymes (SUPERSOMES ™): CYP2C9 & CYP2C19

| Megestrol Acetate | MNC Raw Data Observed (μM) | | Individual Raw Data Observed (μM) | Percent of Parent Disappearance | |
|---|---|---|---|---|---|
| (μM) | Individual | Mean ± SD | | Individual | Mean ± SD |
| Human CYP2C9*1 (Arg$_{144}$) + P450 Reductase + Cytochrome b$_5$ SUPERSOMES ™ - 5 pmol Recombinant Human Cytochrome P450 Enzyme Content | | | | | |
| 5 | 2.24337 | 2.18 ± 0.0589 | 2.09776 | 3.68 | 2.70 ± 0.860 |
|  | 2.16099 |  | 2.12709 | 2.33 |  |
|  | 2.12916 |  | 2.13258 | 2.08 |  |
| 50 | 20.07752 | 25.9 ± 9.13 | 20.37654 | 21.5 | 21.0 ± 1.43 |
|  | 36.46518 |  | 20.18272 | 22.2 |  |
|  | 21.29632 |  | 20.89881 | 19.5 |  |
| Human CYP2C9*1 (Arg$_{144}$) + P450 Reductase + Cytochrome b$_5$ SUPERSOMES ™ - 20 pmol Recombinant Human Cytochrome P450 Enzyme Content | | | | | |
| 5 | 2.79366 | 2.56 ± 0.205 | 2.31398 | 9.53 | 11.0 ± 4.96 |
|  | 2.42217 |  | 2.37894 | 6.99 |  |
|  | 2.45707 |  | 2.13415 | 16.6 |  |
| 50 | 20.38113 | 23.9 ± 3.09 | 24.32507 | −1.60 | 1.19 ± 8.54 |
|  | 25.61708 |  | 21.36306 | 10.8 |  |
|  | 25.82714 |  | 25.28353 | −5.60 |  |
| Human CYP2C19 + P450 Reductase + Cytochrome b$_5$ SUPERSOMES ™ - 5 pmol Recombinant Human Cytochrome P450 Enzyme Content | | | | | |
| 5 | 2.05443 | 1.98 ± 0.0673 | 2.13853 | −8.12 | −3.42 ± 4.34 |
|  | 1.95099 |  | 2.02838 | −2.56 |  |
|  | 1.92810 |  | 1.96934 | 0.430 |  |
| 50 | 19.77224 | 19.5 ± 0.285 | 21.33818 | −9.66 | −4.89 ± 4.16 |
|  | 19.21495 |  | 20.03393 | −2.96 |  |
|  | 19.38658 |  | 19.85772 | −2.05 |  |
| Human CYP2C19 + P450 Reductase + Cytochrome b$_5$ SUPERSOMES ™ - 20 pmol Recombinant Human Cytochrome P450 Enzyme Content | | | | | |
| 5 | 2.29075 | 2.20 ± 0.0797 | 2.14046 | 2.70 | 1.60 ± 2.40 |
|  | 2.16787 |  | 2.22542 | −1.16 |  |
|  | 2.14127 |  | 2.12849 | 3.25 |  |
| 50 | 15.43807 | 15.6 ± 0.121 | 15.71001 | −0.956 | −3.84 ± 2.63 |
|  | 15.56492 |  | 16.25187 | −4.44 |  |
|  | 15.68063 |  | 16.51216 | −6.11 |  |

Abbreviations: SD, standard deviation; MNC, metabolic negative control

Note:

For all calculations above, the resulting values are shown with at least three significant figures for display purposes only.

TABLE 15

Metabolism of Megestrol Acetate in Recombinant Human Cytochrome P450 Enzymes (SUPERSOMES ™): CYP2D6 & CYP2E1

| Megestrol Acetate | MNC Raw Data Observed (μM) | | Individual Raw Data | Percent of Parent Disappearance | |
|---|---|---|---|---|---|
| (μM) | Individual | Mean ± SD | Observed (μM) | Individual | Mean ± SD |
| Human CYP2D6*1 + P450 Reductase SUPERSOMES ™ - 5 pmol Recombinant Human Cytochrome P450 Enzyme Content | | | | | |
| 5 | 1.91014 | 1.98 ± 0.113 | 1.94027 | 1.96 | −13.6 ± 022.0 |
|  | 2.10920 |  | 2.74656 | −38.8 |  |
|  | 1.91782 |  | 2.05569 | −3.87 |  |
| 50 | 16.56077 | 17.7 ± 1.33 | 18.20094 | −3.00 | −10.7 ± 14.2 |
|  | 19.15067 |  | 22.44374 | −27.0 |  |
|  | 17.29879 |  | 18.02901 | −2.03 |  |
| Human CYP2D6*1 + P450 Reductase SUPERSOMES ™ - 20 pmol Recombinant Human Cytochrome P450 Enzyme Content | | | | | |
| 5 | 2.50831 | 2.44 ± 0.0604 | 2.32462 | 4.68 | 2.95 ± 1.50 |
|  | 2.40674 |  | 2.38630 | 2.15 |  |
|  | 2.40097 |  | 2.38955 | 2.01 |  |
| 50 | 12.45675 | 12.7 ± 0.244 | 12.43831 | 1.88 | −1.19 ± 04.14 |
|  | 12.63408 |  | 13.42513 | −5.91 |  |
|  | 12.93864 |  | 12.61961 | 0.449 |  |
| Human CYP2E1 + P450 Reductase + Cytochrome $b_5$ SUPERSOMES ™ - 5 pmol Recombinant Human Cytochrome P450 Enzyme Content | | | | | |
| 5 | 2.85200 | 2.52 ± 0.473 | 2.00754 | 20.4 | 18.5 ± 02.46 |
|  | 1.98173 |  | 2.12587 | 15.8 |  |
|  | 2.73635 |  | 2.03445 | 19.4 |  |
| 50 | 16.30538 | 17.2 ± 1.43 | 21.96732 | −27.8 | −10.5 ± 15.2 |
|  | 18.83310 |  | 17.04136 | 0.853 |  |
|  | 16.42523 |  | 17.98649 | −4.65 |  |
| Human CYP2E1 + P450 Reductase + Cytochrome $b_5$ SUPERSOMES ™ - 20 pmol Recombinant Human Cytochrome P450 Enzyme Content | | | | | |
| 5 | 1.52784 | 1.45 ± 0.0678 | 1.47346 | −1.62 | −7.09 ± 8.42 |
|  | 1.41720 |  | 1.49145 | −2.86 |  |
|  | 1.40473 |  | 1.69332 | −16.8 |  |
| 50 | 20.71697 | 20.8 ± 0.152 | 21.04290 | −1.09 | −2.79 ± 1.69 |
|  | 20.74066 |  | 21.40563 | −2.83 |  |
|  | 20.99169 |  | 21.74434 | −4.46 |  |

Abbreviations: SD, standard deviation; MNC, metabolic negative control
Note:
For all calculations above, the resulting values are shown with at least three significant figures for display purposes only.

TABLE 16

Metabolism of Megestrol Acetate in Recombinant Human Cytochrome P450 Enzymes (SUPERSOMES ™): CYP3A4

| Megestrol Acetate | MNC Raw Data Observed (μM) | | Individual Raw Data | Percent of Parent Disappearance | |
|---|---|---|---|---|---|
| (μM) | Individual | Mean ± SD | Observed (μM) | Individual | Mean ± SD |
| Human CYP3A4 + P450 Reductase + Cytochrome $b_5$ SUPERSOMES ™ - 5 pmol Recombinant Human Cytochrome P450 Enzyme Content | | | | | |
| 5 | 1.99422 | 1.91 ± 0.0710 | 0.80078 | 58.1 | 57.2 ± 02.06 |
|  | 1.87253 |  | 0.79081 | 58.6 |  |
|  | 1.87002 |  | 0.86341 | 54.8 |  |
| 50 | 17.33608 | 18.1 ± 1.01 | 14.29547 | 20.9 | 18.9 ± 1.90 |
|  | 17.65504 |  | 14.66197 | 18.9 |  |
|  | 19.22324 |  | 14.98337 | 17.1 |  |
| Human CYP3A4 + P450 Reductase + Cytochrome $b_5$ SUPERSOMES ™ - 20 pmol Recombinant Human Cytochrome P450 Enzyme Content | | | | | |
| 5 | 1.73474 | 1.56 ± 0.151 | 0.00000[a] | >93.6 | >93.6 ± 0.000 |
|  | 1.48002 |  | 0.00000[a] | >93.6 |  |
|  | 1.46695 |  | 0.00000[a] | >93.6 |  |

TABLE 16-continued

Metabolism of Megestrol Acetate in Recombinant Human Cytochrome P450 Enzymes (SUPERSOMES ™): CYP3A4

| Megestrol Acetate | MNC Raw Data Observed (µM) | | Individual Raw Data | Percent of Parent Disappearance | |
|---|---|---|---|---|---|
| (µM) | Individual | Mean ± SD | Observed (µM) | Individual | Mean ± SD |
| 50 | 19.47176 | 20.1 ± 0.543 | 5.33557 | 73.5 | 70.5 ± 3.89 |
| | 20.35753 | | 5.63074 | 72.0 | |
| | 20.45975 | | 6.81344 | 66.1 | |

Abbreviations: SD, standard deviation; MNC, metabolic negative control
[a] The observed analyzed value (µM) is below the lowest concentration on the standard curve (0.1 µM)
Note:
For all calculations above, the resulting values are shown with at least three significant figures for display purposes only.

Each recombinant human CYP isozyme metabolized specific probe substrates at both 5 and 20 pmol of CYP (Tables 10 and 11). Specifically, specific activity of CYP1A2 was 12.4±0.441 pmol metabolite/minute/pmol CYP and 8.53±0.129 pmol metabolite/minute/pmol CYP, at 5 and 20 pmol CYP1A2, respectively. Specific activity of CYP2A6 was 1.89±0.0434 pmol metabolite/minute/pmol CYP and 1.84±0.0156 pmol metabolite/minute/pmol CYP, at 5 and 20 pmol CYP2A6, respectively. Specific activity of CYP2B6 was 7.40±0.400 pmol metabolite/minute/pmol CYP and 7.58±0.564 pmol metabolite/minute/pmol CYP, at 5 and 20 pmol CYP2B6, respectively. Specific activity of CYP2C8 was 1.68±0.132 pmol metabolite/minute/pmol CYP and 1.17±0.119 pmol metabolite/minute/pmol CYP, at 5 and 20 pmol CYP2C8, respectively. Specific activity of CYP2C9 was 0.992±0.117 pmol metabolite/minute/pmol CYP and 1.14±0.0220 pmol metabolite/minute/pmol CYP, at 5 and 20 pmol CYP2C9, respectively. Specific activity of CYP2C19 was 2.43±0.0380 pmol metabolite/minute/pmol CYP and 1.63±0.0539 pmol metabolite/minute/pmol CYP, at 5 and 20 pmol CYP2C19, respectively. Specific activity of CYP2D6 was 5.46±0.303 pmol metabolite/minute/pmol CYP and 0.837±0.135 pmol metabolite/minute/pmol CYP, at 5 and 20 pmol CYP2D6, respectively. Specific activity of CYP2E1 was 11.6±0.272 pmol metabolite/minute/pmol CYP and 4.16±N/A pmol metabolite/minute/pmol CYP, at 5 and 20 pmol CYP2E1, respectively. And finally specific activity of CYP3A4 was 33.5±3.12 pmol metabolite/minute/pmol CYP and 25.5±0.199 pmol metabolite/minute/pmol CYP, at 5 and 20 pmol CYP3A4, respectively. These data confirmed that each recombinant isozyme preparation was active and suitable for evaluating the metabolism of megestrol acetate.

CYP1A2 does not appear to contribute to megestrol acetate metabolism. When metabolism was measured by depletion of megestrol acetate in the presence of 5 pmol recombinant human CYP1A2, no disappearance of the substrate was detected for either 5 µM or 50 µM substrate concentration (Table 12). The percent of substrate disappearance in the presence of 20 pmol recombinant CYP1A2 was 6.45±1.18 5 for 5 µM substrate, and 7.51±3.06 for 50 µM substrate (Table 12). Conclusions from these results are consistent with those obtained for CYP1A2 in Example 1. The data from the two sets of experiments indicates that CYP1A2 does not metabolize megestrol acetate. This conclusion is further supported by the qualitative analysis of metabolites performed in Example 3. Insignificant metabolism (<1%) occurred based on analysis of metabolites formed in the 50 µM megestrol acetate and 20 pmol CYP1A2 incubations (Table 17). The microsomal incubations with 50 µM megestrol acetate also indicated no significant difference in metabolism in the presence or absence of the inhibitor (Table 18a). Thus, CYP1A2 is not considered to metabolize megestrol acetate.

CYP2A6 may not contribute to megestrol acetate metabolism. The percent of megestrol acetate metabolized by 5 pmol recombinant CYP2A6 was 0.486±4.76 and 1.14±3.38, at 5 µM and 50 µM, respectively (Table 12). The percent of megestrol acetate metabolized by 20 pmol recombinant CYP2A6 was 2.11±4.98 and 1.10±3.16, at 5 µM and 50 µM, respectively (Table 12). This data indicate that CYP2A6 does not metabolize megestrol acetate. These data appear to be contradictory with those obtained in the experiments of Example 1. However, tranylcypromine is not very specific for the inhibition of CYP2A6 and inhibits several other CYPs, including CYP3A4. Thus inhibition of CYP3A4 by tranylcypromine in Example 1 is believed to be the cause of reduced megestrol acetate metabolism. The data from the two sets of experiments together indicate that CYP2A6 does not metabolize megestrol acetate. This conclusion was further supported by the experiments in Example 3 in which a qualitative analysis of metabolites formed in the 50 µM megestrol acetate and 20 pmol CYP2A6 incubations showed that no metabolites were formed (Table 17). The microsomal incubations with 50 µM megestrol acetate indicated a slight difference in metabolism in the presence or absence of the inhibitor (Table 18b), however this is believed to be due to inhibition of CYP3A4 by tranylcypromine, rather than due to inhibition of CYP2A6.

CYP2B6 does not contribute to megestrol metabolism based on the substrate depletion and metabolite formation data. The percent of megestrol acetate metabolized by 5 pmol recombinant CYP2B6 was 2.98±2.20 and 5.73±12.5, at 5 µM and 50 µM, respectively (Table 13). The percent of megestrol acetate metabolized by 20 pmol recombinant CYP2B6 was 2.21±2.14 and 2.53±2.43, at 5 µM and 50 µM, respectively (Table 13). These data indicate that CYP2B6 does not metabolize megestrol acetate. These data are consistent with the experiments of Example 1 indicating that CYP2B6 does not metabolize megestrol acetate. This conclusion is further supported by the experiment in Example 3 in which a qualitative analysis of metabolites formed in the 50 µM megestrol acetate and 20 pmol CYP2B6 incubations showed very little metabolism using mass spectral methods (1.23% metabolites observed; Table 17). The microsomal incubations with 50 µM megestrol acetate indicated no significant difference in metabolism in the presence or absence of the inhibitor (Table 18c). Therefore, CYP2B6 is not believed to metabolize megestrol acetate.

CYP2C8 does not contribute to the metabolism of megestrol acetate. Under all tested substrate or enzyme concentrations, no disappearance of megestrol acetate was detected (Table 13). In addition, only 0.72% of megestrol acetate was converted to its metabolites, which is below the threshold of 1% metabolite formation to be considered significant (Table 17). This conclusion appears to be inconsistent with that obtained in Example 1 and also with the qualitative analysis of metabolites formed in the microsomal incubations with 50 µM megestrol acetate which indicated a significant difference in metabolism in the presence or absence of the inhibitor (Table 18d). However, quercetin, the CYP2C8 selective inhibitor used in Example 1 and Example 3 is not very specific for the inhibition of CYP2C8 and inhibits several other CYPs including CYP3A4. Inhibition of CYP3A4, rather than inhibition of CYP2A6, by quercetin in Examples 1 and 3 is believed to be the cause of the reduced megestrol acetate metabolism observed in those experiments.

The percent of megestrol acetate metabolized by 5 pmol recombinant CYP2C9 was 2.70±0.860 and 21.0±1.43, at 5 µM and 50 µM, respectively (Table 14). The percent of megestrol acetate metabolized by 20 pmol recombinant CYP2C9 was 11.0±4.96 and 1.19±8.54, at 5 µM and 50 µM, respectively (Table 14). These data indicate that CYP2C9 may contribute to the metabolism of megestrol acetate. However, the qualitative analysis of metabolites formed in the 50 µM megestrol acetate and 20 pmol CYP2C9 incubations indicated that megestrol acetate was not metabolized by CYP2C9 (no metabolites observed; Table 17). Furthermore, the qualitative analysis of metabolites formed in the microsomal incubations with 50 µM megestrol acetate also indicated no significant difference in metabolism in the presence or absence of the inhibitor (Table 18e). Therefore, CYP2C9 does not appear to contribute to the metabolism of megestrol acetate.

CYP2C19 does not appear to contribute to megestrol acetate metabolism, based on the formation of a megestrol acetate metabolite by CYP2C19. The percent of megestrol acetate metabolized by 5 pmol recombinant CYP2C19 was 3.42±4.34 and 4.89±4.16, at 5 µM and 50 µM, respectively (Table 14). The percent of megestrol acetate metabolized by 20 pmol recombinant CYP2C19 was 1.60±2.40 and 3.84±2.63, at 5 µM and 50 µM, respectively (Table 14. These data indicate that CYP2C19 does not metabolize megestrol acetate. These data are consistent with the experiments of Example 1 that indicated that CYP2C19 does not metabolize megestrol acetate. In addition, the qualitative analysis in Example 3 of metabolites formed in the 50 µM megestrol acetate and 20 pmol CYP2C19 incubations showed very little metabolite formation (1.14% of metabolites were detected; Table 17). The microsomal incubations with 50 µM megestrol acetate also indicated no significant difference in metabolism in the presence or absence of the inhibitor (Table 18f). Therefore, CYP2C19 is not believed to metabolize megestrol acetate.

CYP2D6 does not contribute to megestrol acetate metabolism. When metabolism was measured by depletion of megestrol acetate, in the presence of 20 pmol CYP2D6 and 5 µM megestrol acetate, the percentage of substrate disappearance was 2.95±2.46, while no substrate disappearance was detected under other substrate or enzyme concentrations (Table 15). This conclusion is consistent with that obtained in Example 1. This conclusion was further supported by the qualitative analysis in Example 3 of metabolites formed in the 50 µM megestrol acetate and 20 pmol CYP2D6 incubations (no metabolites were detected; Table 17). The microsomal incubations with 50 µM megestrol acetate also indicated no significant difference in metabolism in the presence or absence of the inhibitor (Table 18g)

CYP2E1 may not contribute to megestrol acetate metabolism. The percent of megestrol acetate metabolized by 5 pmol recombinant CYP2E1 was 18.5±2.46 and 10.5±15.2, at 5 µM and 50 µM, respectively (Table 15). The percent of megestrol acetate metabolized by 20 pmol recombinant CYP2E1 was 7.09±8.42 and 2.79±1.69, at 5 µM and 50 µM, respectively (Table 15). These data indicate that CYP2E1 does not metabolize megestrol acetate. This conclusion is further supported by the qualitative analysis in Example 3 of metabolites formed in the 50 µM Megestrol acetate and 20 pmol CYP2E1 incubations (no metabolites were detected; Table 17). This data appears to be contradictory with that of Example 1 and the data in Example 3 for the qualitative analysis of microsomal incubations with 50 µM megestrol acetate which indicated a significant difference in metabolism in the presence or absence of the inhibitor (Table 18h). However, diethyldithiocarbamate is not very specific for the inhibition of CYP2E1 and inhibits several other CYPs including CYP3A4. Thus inhibition of CYP3A4 by diethyldithiocarbamate in Examples 1 and 3 is believed to be the cause of the observed results.

CYP3A4 is a cytochrome p450 isozyme metabolizing megestrol acetate. The percent of megestrol acetate metabolized by 5 pmol recombinant CYP3A4 was 57.2±2.06 and 18.9±1.90, at 5 µM and 50 µM, respectively (Table 16). The percent of megestrol acetate metabolized by 20 pmol recombinant CYP3A4 was >93.6±0.000 and 70.5±3.89, at 5 µM and 50 µM, respectively (Table 16). These data indicate that CYP3A4 significantly metabolizes megestrol acetate. This conclusion is consistent with the observations in Example 1 This conclusion was further supported by the qualitative analysis in Example 3 of metabolites formed in the 50 µM megestrol acetate and 20 pmol CYP3A4 incubations (Table 17). More than 50% metabolism of megestrol acetate was observed in incubations with CYP3A4 using mass spectrometric methods. In contrast, incubations with other CYP isoforms resulted in less than or close to 1% metabolism (Table 17). The microsomal incubations with 50 µM megestrol acetate also indicated a significant difference in metabolism in the presence or absence of the inhibitor (Table 18i). This is believed to be due to inhibition of CYP3A4 by ketoconazole. Therefore, CYP3A4 is believed to be the major metabolizing enzyme for megestrol acetate Example 3

Determination of metabolites by LC/MS

Results for determination of megestrol acetate metabolite(s) formed by individual recombinant human CYP isoenzyme at 50 µM megestrol acetate in incubations of SUPERSOMES containing 20 pmol of a cytochrome p450 isozyme measured using liquid chromatography/mass spectrometry (LC/MS; Micromass, Q-T of II) are reported in Table 17. The formation of megestrol acetate metabolite(s) in select microsome incubation samples (50 µM megestrol acetate and 0.5 mg/mL microsomes) in the presence and absence of CYP-selective inhibitors was also qualitatively evaluated by LC/MS. The results are presented in Tables 18a-18f.

When using metabolite formation to assess the extent of metabolism, >10% metabolism of megestrol acetate was considered to be significant metabolism.

TABLE 17

Megestrol Acetate Metabolite formation in Incubation Reactions Containing 50 μM Megestrol Acetate and 20 pmol CYP Enzyme

| Metabolite Name | Formula | m/z Found | Mass Difference (mDa) | Retention Time (min) | Peak Area | Area % |
|---|---|---|---|---|---|---|
| CYP1A2 (Human CYP1A2 + P450 Reductase SUPERSOMES ™) | | | | | | |
| Parent | C24H32O4 | 385.2304 | −7.5 | 25.90 | 6700 | 99.59 |
| Hydroxylation | C24H32O5 | 401.2310 | −1.8 | 19.34 | 27.70 | 0.41 |
| CYP2A6 (Human CYP2A6 + P450 Reductase + Cytochrome $b_5$ SUPERSOMES ™) | | | | | | |
| Parent | C24H32O4 | 385.2303 | −7.6 | 25.92 | 7120.60 | 100.00 |
| CYP2B6 (Human CYP2B6 + P450 Reductase + Cytochrome $b_5$ SUPERSOMES ™) | | | | | | |
| Parent | C24H32O4 | 385.2297 | −8.2 | 25.92 | 7320.20 | 98.77 |
| Hydroxylation | C24H32O5 | 401.2307 | −2.1 | 19.36 | 91.50 | 1.23 |
| CYP2C8 (Human CYP2C8 + P450 Reductase + Cytochrome $b_5$ SUPERSOMES ™) | | | | | | |
| Parent | C24H32O4 | 385.2337 | −4.2 | 25.80 | 7474.90 | 99.28 |
| Hydroxylation | C24H32O5 | 401.2342 | 1.4 | 19.30 | 41.80 | 0.56 |
| Hydroxylation | C24H32O5 | 401.2307 | −2.1 | 21.39 | 12.40 | 0.16 |
| CYP2C9 (Human CYP2C9*1 ($Arg_{144}$) + P450 Reductase + Cytochrome $b_5$ SUPERSOMES ™) | | | | | | |
| Parent | C24H32O4 | 385.2291 | −8.8 | 25.90 | 7088.70 | 100 |
| CYP2C19 (Human CYP2C19 + P450 Reductase + Cytochrome $b_5$ SUPERSOMES ™) | | | | | | |
| Parent | C24H32O4 | 385.2312 | −6.7 | 25.92 | 6306.90 | 98.86 |
| Hydroxylation | C24H32O5 | 401.2327 | −0.1 | 19.34 | 73.00 | 1.14 |
| CYP2D6 (Human CYP2D6*1 + P450 Reductase SUPERSOMES ™) | | | | | | |
| Parent | C24H32O4 | 385.2316 | −6.3 | 25.92 | 5776.40 | 100.00 |
| CYP2E1 (Human CYP2E1 + P450 Reductase + Cytochrome $b_5$ SUPERSOMES ™) | | | | | | |
| Parent | C24H32O4 | 385.2299 | −8.0 | 25.92 | 7274.10 | 100.00 |
| CYP3A4 (Human CYP3A4 + P450 Reductase + Cytochrome $b_5$ SUPERSOMES ™) | | | | | | |
| Parent | C24H32O4 | 385.2320 | −5.9 | 25.90 | 3192.30 | 45.33 |
| Hydroxylation + Oxidation | C24H30O5 | 399.2149 | −2.2 | 22.12 | 353.20 | 5.02 |
| Hydroxylation | C24H32O5 | 401.2280 | −4.8 | 19.34 | 2154.30 | 30.59 |
| Hydroxylation | C24H32O5 | 401.2301 | −2.7 | 20.49 | 269.10 | 3.82 |
| Hydroxylation | C24H32O5 | 401.2308 | −2.0 | 22.30 | 733.00 | 10.41 |
| 2X Hydroxylation | C24H32O6 | 417.2241 | −3.6 | 15.28 | 94.10 | 1.34 |
| 2X Hydroxylation | C24H32O6 | 417.2253 | −2.4 | 16.45 | 192.80 | 2.74 |
| 2X Hydroxylation | C24H32O6 | 417.2257 | −2.0 | 17.28 | 9.90 | 0.14 |
| 2X Hydroxylation | C24H32O6 | 417.2239 | −3.8 | 18.02 | 35.90 | 0.51 |
| 2X Hydroxylation | C24H32O6 | 417.2261 | −1.6 | 18.60 | 8.00 | 0.11 |

TABLE 18a

Metabolynx Report for Incubation Containing 50 μM Megestrol Acetate and 0.5 mg/mL Microsomes: CYP1A2

| Metabolite Name | Formula | m/z Found | Mass Difference (mDa) | Retention Time (min) | Peak Area | Area % |
|---|---|---|---|---|---|---|
| CYP1A2 (Pooled human liver microsomes with 1% acetonitrile) | | | | | | |
| Parent | C24H32O4 | 385.2367 | −1.2 | 25.82 | 4187.80 | 69.94 |
| Hydroxylation + Oxidation | C24H30O5 | 399.2184 | 1.3 | 22.06 | 61.20 | 1.02 |
| Hydroxylation | C24H32O5 | 401.2346 | 1.8 | 19.30 | 1281.7 | 21.41 |
| Hydroxylation | C24H32O5 | 401.2334 | 0.6 | 20.43 | 99.50 | 1.66 |
| Hydroxylation | C24H32O5 | 401.2320 | −0.8 | 21.39 | 32.00 | 0.53 |
| Hydroxylation | C24H32O5 | 401.2335 | 0.7 | 22.14 | 248.00 | 4.14 |
| 2X Hydroxylation | C24H32O6 | 417.2288 | 1.1 | 15.24 | 16.20 | 0.27 |
| 2X Hydroxylation | C24H32O6 | 417.2286 | 0.9 | 16.39 | 49.10 | 0.82 |
| 2X Hydroxylation | C24H32O6 | 417.2292 | 1.5 | 17.99 | 12.00 | 0.20 |
| CYP1A2 (Pooled human liver microsomes with 5 μM Furafylline) | | | | | | |
| Parent | C24H32O4 | 385.2383 | 0.4 | 25.82 | 4069.90 | 67.32 |
| Hydroxylation + Oxidation | C24H30O5 | 399.2183 | 1.2 | 22.02 | 63.50 | 1.05 |
| Hydroxylation | C24H32O5 | 401.2320 | −0.8 | 19.30 | 1413.00 | 23.37 |
| Hydroxylation | C24H32O5 | 401.2338 | 1.0 | 20.43 | 109.90 | 1.82 |

TABLE 18a-continued

Metabolynx Report for Incubation Containing
50 μM Megestrol Acetate and 0.5 mg/mL Microsomes: CYP1A2

| Metabolite Name | Formula | m/z Found | Mass Difference (mDa) | Retention Time (min) | Peak Area | Area % |
|---|---|---|---|---|---|---|
| Hydroxylation | C24H32O5 | 401.2345 | 1.7 | 22.14 | 272.00 | 4.50 |
| Hydroxylation | C24H32O5 | 401.2358 | 3.0 | 21.39 | 35.00 | 0.58 |
| 2X Hydroxylation | C24H32O6 | 417.2277 | 0.0 | 16.39 | 52.70 | 0.87 |
| 2X Hydroxylation | C24H32O6 | 417.2281 | 0.4 | 17.99 | 13.40 | 0.22 |
| 2X Hydroxylation | C24H32O6 | 417.2289 | 1.2 | 15.24 | 16.00 | 0.26 |

TABLE 18b

Metabolynx Report for Incubation Containing
50 μM Megestrol Acetate and 0.5 mg/mL Microsomes: CYP2A6

| Metabolite Name | Formula | m/z Found | Mass Difference (mDa) | Retention Time (min) | Peak Area | Area % |
|---|---|---|---|---|---|---|
| CYP2A6 (Pooled human liver microsomes with 1% water) | | | | | | |
| Parent | C24H32O4 | 385.2372 | −0.7 | 25.83 | 2932.40 | 59.79 |
| Hydroxylation + Oxidation | C24H30O5 | 399.2180 | 0.9 | 22.06 | 87.20 | 1.78 |
| Hydroxylation | C24H32O5 | 401.2329 | 0.1 | 19.30 | 1322.00 | 26.96 |
| Hydroxylation | C24H32O5 | 401.2332 | 0.4 | 22.16 | 274.30 | 5.59 |
| Hydroxylation | C24H32O5 | 401.2335 | 0.7 | 20.43 | 101.40 | 2.07 |
| Hydroxylation | C24H32O5 | 401.2338 | 1.0 | 21.40 | 33.00 | 0.67 |
| 2X Hydroxylation | C24H32O6 | 417.2257 | −2.0 | 17.99 | 32.40 | 0.66 |
| 2X Hydroxylation | C24H32O6 | 417.2275 | −0.2 | 16.39 | 76.00 | 1.55 |
| 2X Hydroxylation | C24H32O6 | 417.2300 | 2.3 | 15.24 | 26.50 | 0.54 |
| S-Glutathione Conjugation | C34H47N3O10S | 690.3023 | −3.7 | 14.95 | 19.20 | 0.39 |
| CYP2A6 (Pooled human liver microsomes with 10 μM Tranylcypromine) | | | | | | |
| Parent | C24H32O4 | 385.2380 | 0.1 | 25.83 | 2270.20 | 65.31 |
| Hydroxylation + Oxidation | C24H30O5 | 399.2175 | 0.4 | 22.06 | 41.70 | 1.20 |
| Hydroxylation | C24H32O5 | 401.2334 | 0.6 | 22.17 | 161.60 | 4.65 |
| Hydroxylation | C24H32O5 | 401.2340 | 1.2 | 19.30 | 859.80 | 24.74 |
| Hydroxylation | C24H32O5 | 401.2342 | 1.4 | 21.40 | 27.70 | 0.80 |
| Hydroxylation | C24H32O5 | 401.2346 | 1.8 | 20.45 | 49.80 | 1.43 |
| 2X Hydroxylation | C24H32O6 | 417.2282 | 0.5 | 15.26 | 12.10 | 0.35 |
| 2X Hydroxylation | C24H32O6 | 417.2285 | 0.8 | 16.39 | 36.90 | 1.06 |
| 2X Hydroxylation | C24H32O6 | 417.2307 | 3.0 | 17.99 | 16.10 | 0.46 |

TABLE 18c

Metabolynx Report for Incubation Containing
50 μM Megestrol Acetate and 0.5 mg/mL Microsomes: CYP2B6

| Metabolite Name | Formula | m/z Found | Mass Difference (mDa) | Retention Time (min) | Peak Area | Area % |
|---|---|---|---|---|---|---|
| CYP2B6 (Pooled human liver microsomes with 1% methanol) | | | | | | |
| Parent | C24H32O4 | 385.2372 | −0.7 | 25.82 | 2924.70 | 63.45 |
| Hydroxylation + Oxidation | C24H30O5 | 399.2172 | 0.1 | 22.06 | 61.80 | 1.34 |
| Hydroxylation | C24H32O5 | 401.2314 | −1.4 | 21.40 | 31.80 | 0.69 |
| Hydroxylation | C24H32O5 | 401.2325 | −0.3 | 22.17 | 247.00 | 5.36 |
| Hydroxylation | C24H32O5 | 401.2329 | 0.1 | 19.30 | 1167.20 | 25.32 |
| Hydroxylation | C24H32O5 | 401.2332 | 0.4 | 20.43 | 81.10 | 1.76 |
| 2X Hydroxylation | C24H32O6 | 417.2279 | 0.2 | 16.39 | 55.60 | 1.21 |
| 2X Hydroxylation | C24H32O6 | 417.2282 | 0.5 | 15.24 | 14.60 | 0.32 |
| 2X Hydroxylation | C24H32O6 | 417.2303 | 2.6 | 17.99 | 26.00 | 0.56 |
| CYP2B6 (Pooled human liver microsomes with 1 μM Ticlopidine) | | | | | | |
| Parent | C24H32O4 | 385.2375 | −0.4 | 25.82 | 26.09.50 | 63.04 |
| Hydroxylation + Oxidation | C24H30O5 | 399.2183 | 1.2 | 22.06 | 58.70 | 1.42 |
| Hydroxylation | C24H32O5 | 401.2327 | −0.1 | 19.30 | 1040.60 | 25.14 |
| Hydroxylation | C24H32O5 | 401.2332 | 0.4 | 20.45 | 68.30 | 1.65 |

TABLE 18c-continued

Metabolynx Report for Incubation Containing
50 μM Megestrol Acetate and 0.5 mg/mL Microsomes: CYP2B6

| Metabolite Name | Formula | m/z Found | Mass Difference (mDa) | Retention Time (min) | Peak Area | Area % |
|---|---|---|---|---|---|---|
| Hydroxylation | C24H32O5 | 401.2345 | 1.7 | 21.40 | 27.50 | 0.66 |
| Hydroxylation | C24H32O5 | 401.2346 | 1.8 | 22.19 | 248.00 | 5.99 |
| 2X Hydroxylation | C24H32O6 | 417.2279 | 0.2 | 17.99 | 23.90 | 0.58 |
| 2X Hydroxylation | C24H32O6 | 417.2306 | 2.9 | 16.39 | 50.60 | 1.22 |
| 2X Hydroxylation | C24H32O6 | 417.2315 | 3.8 | 15.24 | 12.30 | 0.30 |

TABLE 18d

Metabolynx Report for Incubation Containing
50 μM Megestrol Acetate and 0.5 mg/mL Microsomes: CYP2C8

| Metabolite Name | Formula | m/z Found | Mass Difference (mDa) | Retention Time (min) | Peak Area | Area % |
|---|---|---|---|---|---|---|
| CYP2C8 (Pooled human liver microsomes with 0.1% DMSO) | | | | | | |
| Parent | C24H32O4 | 385.2371 | −0.8 | 25.83 | 4151.30 | 69.53 |
| Hydroxylation + Oxidation | C24H30O5 | 399.2190 | 1.9 | 22.06 | 63.30 | 1.06 |
| Hydroxylation | C24H32O5 | 401.2321 | −0.7 | 19.30 | 1322.60 | 22.15 |
| Hydroxylation | C24H32O5 | 401.2333 | 0.5 | 21.41 | 31.60 | 0.53 |
| Hydroxylation | C24H32O5 | 401.2341 | 1.3 | 20.45 | 109.70 | 1.84 |
| Hydroxylation | C24H32O5 | 401.2347 | 1.9 | 22.23 | 180.10 | 3.02 |
| 2X Hydroxylation | C24H32O6 | 417.2276 | −0.1 | 17.99 | 41.10 | 0.69 |
| 2X Hydroxylation | C24H32O6 | 417.2277 | 0.0 | 16.39 | 39.70 | 0.66 |
| 2X Hydroxylation | C24H32O6 | 417.2282 | 0.5 | 15.26 | 21.30 | 0.36 |
| S−Glutathione Conjugation | C34H47N3O10S | 690.3013 | −4.7 | 14.98 | 10.10 | 0.17 |
| CYP2C8 (Pooled human liver microsomes with 100 μM Quercetin) | | | | | | |
| Parent | C24H32O4 | 385.2362 | −1.7 | 25.82 | 5734.70 | 99.11 |
| Hydroxylation | C24H32O5 | 401.2312 | −1.6 | 19.30 | 51.70 | 0.89 |

TABLE 18e

Metabolynx Report for Incubation Containing
50 μM Megestrol Acetate and 0.5 mg/mL Microsomes: CYP2C9

| Metabolite Name | Formula | m/z Found | Mass Difference (mDa) | Retention Time (min) | Peak Area | Area % |
|---|---|---|---|---|---|---|
| CYP2C9 (Pooled human liver microsomes with 1% acetonitrile) | | | | | | |
| Parent | C24H32O4 | 385.2383 | 0.4 | 25.82 | 3073.50 | 63.17 |
| Hydroxylation + Oxidation | C24H30O5 | 399.2170 | −0.1 | 22.06 | 67.50 | 1.39 |
| Hydroxylation | C24H32O5 | 401.2329 | 0.1 | 22.23 | 284.20 | 5.84 |
| Hydroxylation | C24H32O5 | 401.2330 | 0.2 | 19.30 | 1221.80 | 25.11 |
| Hydroxylation | C24H32O5 | 401.2340 | 1.2 | 20.45 | 100.60 | 2.07 |
| Hydroxylation | C24H32O5 | 401.2343 | 1.5 | 21.40 | 34.10 | 0.70 |
| 2X Hydroxylation | C24H32O6 | 417.2269 | −0.8 | 16.39 | 58.70 | 1.21 |
| 2X Hydroxylation | C24H32O6 | 417.2289 | 1.2 | 17.99 | 25.20 | 0.52 |
| CYP2C9 (Pooled human liver microsomes with 1.5 μM Sulfaphenazole) | | | | | | |
| Parent | C24H32O4 | 385.2357 | −2.2 | 25.82 | 3459.60 | 64.68 |
| Hydroxylation + Oxidation | C24H30O5 | 399.2177 | 0.6 | 22.06 | 62.90 | 1.18 |
| Hydroxylation | C24H32O5 | 401.2331 | 0.3 | 19.30 | 1316.30 | 24.61 |
| Hydroxylation | C24H32O5 | 401.2331 | 0.3 | 21.40 | 37.90 | 0.71 |
| Hydroxylation | C24H32O5 | 401.2349 | 2.1 | 22.23 | 276.20 | 5.16 |
| Hydroxylation | C24H32O5 | 401.2354 | 2.6 | 20.45 | 110.00 | 2.06 |
| 2X Hydroxylation | C24H32O6 | 417.2286 | 0.9 | 17.99 | 24.80 | 0.46 |
| 2X Hydroxylation | C24H32O6 | 417.2305 | 2.8 | 16.41 | 61.40 | 1.15 |

TABLE 18f

Metabolynx Report for Incubation Containing
50 μM Megestrol Acetate and 0.5 mg/mL Microsomes: CYP2C19

| Metabolite Name | Formula | m/z Found | Mass Difference (mDa) | Retention Time (min) | Peak Area | Area % |
|---|---|---|---|---|---|---|
| CYP2C19 (Pooled human liver microsomes with 1% methanol) ||||||| 
| Parent | C24H32O4 | 385.2376 | −0.3 | 25.80 | 3930.50 | 66.31 |
| Hydroxylation + Oxidation | C24H30O5 | 399.2191 | 2.0 | 22.02 | 66.10 | 1.12 |
| Hydroxylation | C24H32O5 | 401.2327 | −0.1 | 20.43 | 100.90 | 1.70 |
| Hydroxylation | C24H32O5 | 401.2331 | 0.3 | 19.30 | 1399.60 | 23.61 |
| Hydroxylation | C24H32O5 | 401.2345 | 1.7 | 21.39 | 35.50 | 0.60 |
| Hydroxylation | C24H32O5 | 401.2347 | 1.9 | 22.19 | 300.70 | 5.07 |
| 2X Hydroxylation | C24H32O6 | 417.2287 | 1.0 | 16.39 | 60.60 | 1.02 |
| 2X Hydroxylation | C24H32O6 | 417.2289 | 1.2 | 17.98 | 33.40 | 0.56 |
| 2X Hydroxylation | C24H32O6 | | | | | |
| CYP2C19 (Pooled human liver microsomes with 80 μM Nootkatone) ||||||| 
| Parent | C24H32O4 | 385.2378 | −0.1 | 25.81 | 4081.30 | 67.75 |
| Hydroxylation + Oxidation | C24H30O5 | 399.2176 | 0.5 | 122.02 | 44.80 | 0.74 |
| Hydroxylation | C24H32O5 | 401.2328 | 0.0 | 19.30 | 1445.60 | 24.00 |
| Hydroxylation | C24H32O5 | 401.2333 | 0.5 | 21.40 | 28.20 | 0.47 |
| Hydroxylation | C24H32O5 | 401.2337 | 0.9 | 20.43 | 93.30 | 1.55 |
| Hydroxylation | C24H32O5 | 401.2341 | 1.3 | 22.23 | 269.70 | 4.48 |
| 2X Hydroxylation | C24H32O6 | 417.2272 | −0.5 | 16.39 | 41.30 | 0.69 |
| 2X Hydroxylation | C24H32O6 | 417.2286 | 0.9 | 17.99 | 19.90 | 0.33 |

TABLE 18g

Metabolynx Report for Incubation Containing
50 μM Megestrol Acetate and 0.5 mg/mL Microsomes: CYP2D6

| Metabolite Name | Formula | m/z Found | Mass Difference (mDa) | Retention Time (min) | Peak Area | Area % |
|---|---|---|---|---|---|---|
| CYP2D6 (Pooled human liver microsomes with 1% methanol) |||||||
| Parent | C24H32O4 | 385.2369 | −1.0 | 25.81 | 3988 | 66.93 |
| Hydroxylation + Oxidation | C24H30O5 | 399.2192 | 2.1 | 22.02 | 67.10 | 1.13 |
| Hydroxylation | C24H32O5 | 401.2325 | −0.3 | 19.30 | 1386.30 | 23.26 |
| Hydroxylation | C24H32O5 | 401.2334 | 0.6 | 21.36 | 32.50 | 0.55 |
| Hydroxylation | C24H32O5 | 401.2337 | 0.9 | 22.19 | 296.20 | 4.97 |
| Hydroxylation | C24H32O5 | 401.2344 | 1.6 | 20.43 | 105.20 | 1.77 |
| 2X Hydroxylation | C24H32O6 | 417.2275 | −0.2 | 16.39 | 54.90 | 0.92 |
| 2X Hydroxylation | C24H32O6 | 417.2299 | 2.2 | 17.99 | 28.60 | 0.48 |
| CYP2A6 (Pooled human liver microsomes with 10 μM Tranylcypromine) |||||||
| Parent | C24H32O4 | 385.2372 | −0.7 | 25.81 | 4039.50 | 67.40 |
| Hydroxylation + Oxidation | C24H30O5 | 399.2168 | −0.3 | 22.02 | 69.80 | 1.16 |
| Hydroxylation | C24H32O5 | 401.2323 | −0.5 | 21.40 | 34.80 | 0.58 |
| Hydroxylation | C24H32O5 | 401.2325 | −0.3 | 22.19 | 306.20 | 5.11 |
| Hydroxylation | C24H32O5 | 401.2335 | 0.7 | 19.30 | 1435.30 | 23.95 |
| Hydroxylation | C24H32O5 | 401.2338 | 1.0 | 20.43 | 107.60 | 1.80 |

TABLE 18h

Metabolynx Report for Incubation Containing
50 μM Megestrol Acetate and 0.5 mg/mL Microsomes: CYP2E1

| Metabolite Name | Formula | m/z Found | Mass Difference (mDa) | Retention Time (min) | Peak Area | Area % |
|---|---|---|---|---|---|---|
| CYP2E1 (Pooled human liver microsomes with 1% water) |||||||
| Parent | C24H32O4 | 385.2374 | −0.5 | 25.82 | 3520.60 | 59.79 |
| Hydroxylation + Oxidation | C24H30O5 | 399.2180 | 0.9 | 22.06 | 94.40 | 1.60 |
| Hydroxylation | C24H32O5 | 401.2319 | −0.9 | 19.32 | 1582.80 | 26.88 |
| Hydroxylation | C24H32O5 | 401.2332 | 0.4 | 20.45 | 122.20 | 2.08 |

TABLE 18h-continued

Metabolynx Report for Incubation Containing
50 μM Megestrol Acetate and 0.5 mg/mL Microsomes: CYP2E1

| Metabolite Name | Formula | m/z Found | Mass Difference (mDa) | Retention Time (min) | Peak Area | Area % |
|---|---|---|---|---|---|---|
| Hydroxylation | C24H32O5 | 401.2343 | 1.5 | 22.23 | 385.40 | 6.55 |
| Hydroxylation | C24H32O5 | 401.2347 | 1.9 | 21.40 | 38.90 | 0.66 |
| 2X Hydroxylation | C24H32O6 | 417.2282 | 0.5 | 17.99 | 54.00 | 0.92 |
| 2X Hydroxylation | C24H32O6 | 417.2285 | 0.8 | 16.41 | 89.70 | 1.52 |
| CYP2E1 (Pooled human liver microsomes with 100 μM Diethyldithiocarbamate) | | | | | | |
| Parent | C24H32O4 | 385.2375 | −0.4 | 25.82 | 5225.10 | 90.95 |
| Hydroxylation | C24H32O5 | 401.2329 | 0.1 | 19.30 | 424.30 | 7.39 |
| Hydroxylation | C24H32O5 | 401.2332 | 0.4 | 21.40 | 23.20 | 0.40 |
| Hydroxylation | C24H32O5 | 401.2341 | 1.3 | 20.45 | 16.10 | 0.28 |
| Hydroxylation | C24H32O5 | 401.2342 | 1.4 | 22.28 | 56.20 | 0.98 |

TABLE 18i

Metabolynx Report for Incubation Containing
50 μM Megestrol Acetate and 0.5 mg/mL Microsomes: CYP3A4

| Metabolite Name | Formula | m/z Found | Mass Difference (mDa) | Retention Time (min) | Peak Area | Area % |
|---|---|---|---|---|---|---|
| CYP3A4 (Pooled human liver microsomes with 1% acetonitrile) | | | | | | |
| Parent | C24H32O4 | 385.2369 | −1.0 | 25.82 | 3823.80 | 63.38 |
| Hydroxylation + Oxidation | C24H30O5 | 399.2173 | 0.2 | 22.06 | 71.30 | 1.18 |
| Hydroxylation | C24H32O5 | 401.2325 | −0.3 | 22.23 | 365.00 | 6.05 |
| Hydroxylation | C24H32O5 | 401.2327 | −0.1 | 19.30 | 1514.20 | 25.10 |
| Hydroxylation | C24H32O5 | 401.2334 | 0.6 | 20.43 | 121.90 | 2.02 |
| Hydroxylation | C24H32O5 | 401.2339 | 1.1 | 21.40 | 38.90 | 0.64 |
| 2X Hydroxylation | C24H32O6 | 417.2282 | 0.5 | 16.39 | 68.60 | 1.14 |
| 2X Hydroxylation | C24H32O6 | 417.2287 | 1.0 | 17.99 | 29.30 | 0.49 |
| CYP3A4 (Pooled human liver microsomes with 1 μM Ketoconazole) | | | | | | |
| Parent | C24H32O4 | 385.2377 | −0.2 | 25.82 | 4787.00 | 95.21 |
| Hydroxylation + Oxidation | C24H30O5 | 401.2325 | −0.3 | 19.30 | 180.10 | 3.50 |
| Hydroxylation | C24H32O5 | 401.2342 | 1.4 | 21.40 | 37.70 | 0.75 |

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A method of administering megestrol acetate, comprising
    administering megestrol acetate to a patient in need of megestrol acetate therapy;
    determining that a substance that is an inhibitor or an inducer of CYP3A4 is coadministered to the patient;
    monitoring the patient's plasma concentration of megestrol acetate;
    determining that the patient experiences an adverse reaction associated with elevated or decreased megestrol acetate plasma concentration during coadministration of megestrol acetate and the substance; and
    adjusting administration of megestrol acetate or the substance to the patient to reduce severity of or eliminate the adverse reaction.

2. The method of claim 1, wherein the substance is an inhibitor of CYP3A4, the patient experiences an adverse reaction associated with elevated megestrol acetate plasma concentration, and adjusting administration comprises
    ceasing to administer the inhibitor or megestrol acetate.

3. The method of claim 1, wherein the substance is an inducer of CYP3A4, the patient experiences an adverse reaction associated with reduced megestrol acetate plasma concentration, and adjusting administration comprises
    ceasing to administer the inducer; or
    increasing the dosage of megestrol acetate.

4. A method of avoiding an adverse event when administering megestrol acetate, comprising
    determining that a patient in need of megestrol acetate therapy is taking a substance that is a known inhibitor or a known inducer of CYP3A4;
    monitoring the patient's plasma concentration of megestrol acetate; and
    adjusting administration to the patient of megestrol acetate or the substance to avoid an adverse event associated with a change in the metabolism of megestrol acetate, wherein the adjusting administration comprises ceasing to administer the substance if the substance is an inducer of CYP3A4 or increasing the dosage of megestrol acetate if the substance is an inhibitor of CYP3A4.

5. The method of claim 4, wherein the substance which is a known inhibitor of CYP3A4 is delavirdine, indinavir, nelfinavir, ritonavir, amiodarone, aprepitant, cinchloramphenicol, cimetidine, clarithromycin, diethyl-dithiocarbamate, diltiazem, erythromycin, fluconazole, fluvoxamine, gestodene, grapefruit juice, Seville orange juice, imatinib, itraconazole, ketoconazole, mifepristone, nefazodone, norfloxacin, norfluoxetine, mibefradil, star fruit, verapamil, or voriconazole.

6. The method of claim 4, wherein the substance which is a known inducer of CYP3A4 is barbiturates, carbamazepine, efavirenz, glucocorticoids, modafinil, nevirapine, phenobarbital, phenyloin, rifampin, St. John's wort, troglitazone, oxcarbazepine, pioglitazone, or rifabutin.

* * * * *